United States Patent
Rotem

(10) Patent No.: US 12,285,228 B2
(45) Date of Patent: Apr. 29, 2025

(54) SURGICAL ROBOTIC POSITIONING CART

(71) Applicant: Momentis Surgical LTD, Or Yehuda (IL)

(72) Inventor: Idan Rotem, Tel Aviv (IL)

(73) Assignee: Momentis Surgical Ltd, Or-Yehuda (IL)

( * ) Notice: Subject to any disclaimer, the term of this patent is extended or adjusted under 35 U.S.C. 154(b) by 276 days.

(21) Appl. No.: 17/890,301

(22) Filed: Aug. 18, 2022

(65) Prior Publication Data

US 2023/0090944 A1 Mar. 23, 2023

Related U.S. Application Data

(63) Continuation-in-part of application No. PCT/IL2021/050188, filed on Feb. 17, 2021.

(30) Foreign Application Priority Data

Feb. 20, 2020 (IL) .......................................... 272830

(51) Int. Cl.
*A61B 8/00* (2006.01)
*A61B 34/30* (2016.01)

(52) U.S. Cl.
CPC ........ *A61B 34/30* (2016.02); *A61B 2034/304* (2016.02); *A61B 2034/306* (2016.02); *A61B 2560/0437* (2013.01)

(58) Field of Classification Search
CPC .............. A61B 34/30; A61B 2034/304; A61B 2034/306; A61B 2560/0437;
(Continued)

(56) References Cited

U.S. PATENT DOCUMENTS 6,493,220 B1 * 12/2002 Clark .................... A61B 5/0002
361/679.41
6,723,106 B1 4/2004 Charles
(Continued)

FOREIGN PATENT DOCUMENTS

GB 2504843 A 2/2014
JP 2006141976 A 6/2006
(Continued)

OTHER PUBLICATIONS

Applicant response in accordance with regulation 36 2 filed in Israel patent office Jan. 4, 2021 in IL 272830.
(Continued)

*Primary Examiner* — Amy J. Sterling
(74) *Attorney, Agent, or Firm* — Momentum IP; Marc Van Dyke

(57) ABSTRACT

A surgical positioning cart configured to support a surgical robotic device thereon a distal side configured to face a surgical entry site of a patient, comprises a base movable at least along a horizontal reference plane, a head pivotable relative to the horizontal plane to define therewith different inclination angles at least in a plane comprising vertical and longitudinal axes of the cart; a slider configured to fixedly receive at least a portion of the surgical robotic device thereon and mounted to the head so as to be pivotable therewith and be movable relative thereto at least along the longitudinal axis; and a neck connecting between the base and the head pivotally mounted thereto, having an adjustable height defined by a length of the neck in the vertical direction.

22 Claims, 15 Drawing Sheets

(58) Field of Classification Search
CPC ...... A61B 2034/2048; A61B 2034/302; A61B 2090/508; A61B 90/50; A61B 50/13
See application file for complete search history.

(56) References Cited

U.S. PATENT DOCUMENTS

| | | | |
|---|---|---|---|
| 7,766,821 B2 | 8/2010 | Brunnen | |
| 7,833,150 B2 | 11/2010 | Yamamoto | |
| 8,378,620 B2* | 2/2013 | Reckelhoff | A61G 12/001 |
| | | | 320/101 |
| 8,506,555 B2 | 8/2013 | Ruiz Morales | |
| 8,692,140 B1* | 4/2014 | Pollock | A61B 50/37 |
| | | | 177/15 |
| 9,039,057 B2 | 5/2015 | Schvalb | |
| 9,788,911 B2 | 10/2017 | Cohen | |
| 9,820,822 B2 | 11/2017 | Cohen | |
| 10,022,196 B2 | 7/2018 | Griffiths et al. | |
| 10,022,197 B2 | 7/2018 | Cohen | |
| 10,052,165 B2 | 8/2018 | Cohen | |
| 10,070,930 B2 | 9/2018 | Cohen | |
| 10,299,866 B2 | 5/2019 | Cohen | |
| 10,470,831 B2 | 11/2019 | Cohen | |
| 10,500,003 B2 | 12/2019 | Cohen | |
| 10,617,481 B2 | 4/2020 | Cohen | |
| 10,736,658 B2 | 8/2020 | Cohen | |
| 10,849,654 B2 | 12/2020 | Cohen | |
| 10,869,692 B2 | 12/2020 | Cohen | |
| 10,973,592 B2 | 4/2021 | Cohen | |
| 2007/0055103 A1 | 3/2007 | Hoefig | |
| 2009/0247993 A1 | 10/2009 | Kirschenman | |
| 2011/0313245 A1 | 12/2011 | Scholly | |
| 2012/0186383 A1 | 7/2012 | Schvalb | |
| 2012/0212116 A1* | 8/2012 | McRorie | A61B 50/13 |
| | | | 312/249.13 |
| 2014/0088361 A1 | 3/2014 | Hrayr | |
| 2015/0297282 A1* | 10/2015 | Cadouri | A61B 18/1492 |
| | | | 606/34 |
| 2015/0327940 A1 | 11/2015 | Inoue | |
| 2016/0080701 A1 | 3/2016 | Henn | |
| 2016/0143633 A1 | 5/2016 | Robert | |
| 2016/0213435 A1 | 7/2016 | Hourtash | |
| 2016/0242860 A1 | 8/2016 | Diolaiti | |
| 2017/0071687 A1 | 3/2017 | Cohen | |
| 2017/0071688 A1 | 3/2017 | Cohen | |
| 2017/0079731 A1 | 3/2017 | Griffiths | |
| 2017/0086932 A1 | 3/2017 | Auld | |
| 2017/0112581 A1 | 4/2017 | Cohen | |
| 2017/0112583 A1 | 4/2017 | Cohen | |
| 2017/0119483 A1 | 5/2017 | Cohen | |
| 2017/0135776 A1 | 5/2017 | Cohen | |
| 2017/0231701 A1 | 8/2017 | Cohen | |
| 2017/0239005 A1 | 8/2017 | Cohen | |
| 2017/0258538 A1 | 9/2017 | Cohen | |
| 2017/0258539 A1 | 9/2017 | Cohen | |
| 2017/0334067 A1 | 11/2017 | Swarup | |
| 2018/0256235 A1 | 9/2018 | Cohen | |
| 2018/0256241 A1 | 9/2018 | Cohen | |
| 2018/0256246 A1 | 9/2018 | Cohen | |
| 2018/0256265 A1 | 9/2018 | Cohen | |
| 2018/0256266 A1 | 9/2018 | Cohen | |
| 2018/0256267 A1 | 9/2018 | Cohen | |
| 2018/0256268 A1 | 9/2018 | Cohen | |
| 2018/0280095 A1* | 10/2018 | Lattimore | A61B 90/50 |
| 2019/0000574 A1 | 1/2019 | Cohen | |
| 2019/0059868 A1 | 2/2019 | Cohen | |
| 2019/0059939 A1 | 2/2019 | Cohen | |
| 2019/0059940 A1 | 2/2019 | Cohen | |
| 2019/0059941 A1 | 2/2019 | Cohen | |
| 2019/0083193 A1 | 3/2019 | Cohen | |
| 2019/0167363 A1 | 6/2019 | Cohen | |
| 2019/0167364 A1 | 6/2019 | Cohen | |
| 2019/0231445 A1 | 8/2019 | Cohen | |
| 2020/0289225 A1 | 9/2020 | Cohen | |
| 2021/0059716 A1 | 3/2021 | Cohen | |
| 2021/0196407 A1 | 7/2021 | Cohen | |
| 2021/0236234 A1 | 8/2021 | Cohen | |
| 2021/0259796 A1* | 8/2021 | Danilkin | A61B 50/13 |
| 2021/0338345 A1 | 11/2021 | Cohen | |
| 2022/0054205 A1 | 2/2022 | Cohen | |
| 2023/0000571 A1 | 1/2023 | Cohen | |
| 2023/0000579 A1 | 1/2023 | Cohen | |
| 2023/0255596 A1* | 8/2023 | Chamberlain | A61B 8/461 |
| | | | 600/437 |
| 2024/0058079 A1* | 2/2024 | Kim | A61B 34/70 |
| 2024/0206995 A1* | 6/2024 | Boonzaier | A61B 34/30 |
| 2024/0207654 A1* | 6/2024 | Xu | A61N 7/00 |

FOREIGN PATENT DOCUMENTS

| | | |
|---|---|---|
| JP | 2009525098 A | 7/2009 |
| WO | 2016/069663 A1 | 5/2016 |
| WO | 2020/185516 A1 | 9/2020 |
| WO | 2021/165963 A1 | 8/2021 |

OTHER PUBLICATIONS

Auris Surgical Robotics MONARCH™ Platform User Manual [manual dated May 8, 2018].
International Search Report for PCT/IL2021/050188 document completed Mar. 8, 2021.
Intuitive website page (En-US products-and-services/da-vinci/systems) downloaded on Apr. 5, 2023.
Mako Total Knee Toolkit [guide dated 2017].
MedroboticCorp.Flex RoboticSystem Brochure [brochure dated 2016].
ROSA One Brain Application Brochure [brochure dated 2019].
Senhance Brochure (EU) from Transenterix [brochure dated Aug. 2019].
Titan Medical Investor Presentation May 2018.
Written Opinion for PCT/IL2021/050188 document completed Mar. 8, 2021.

* cited by examiner

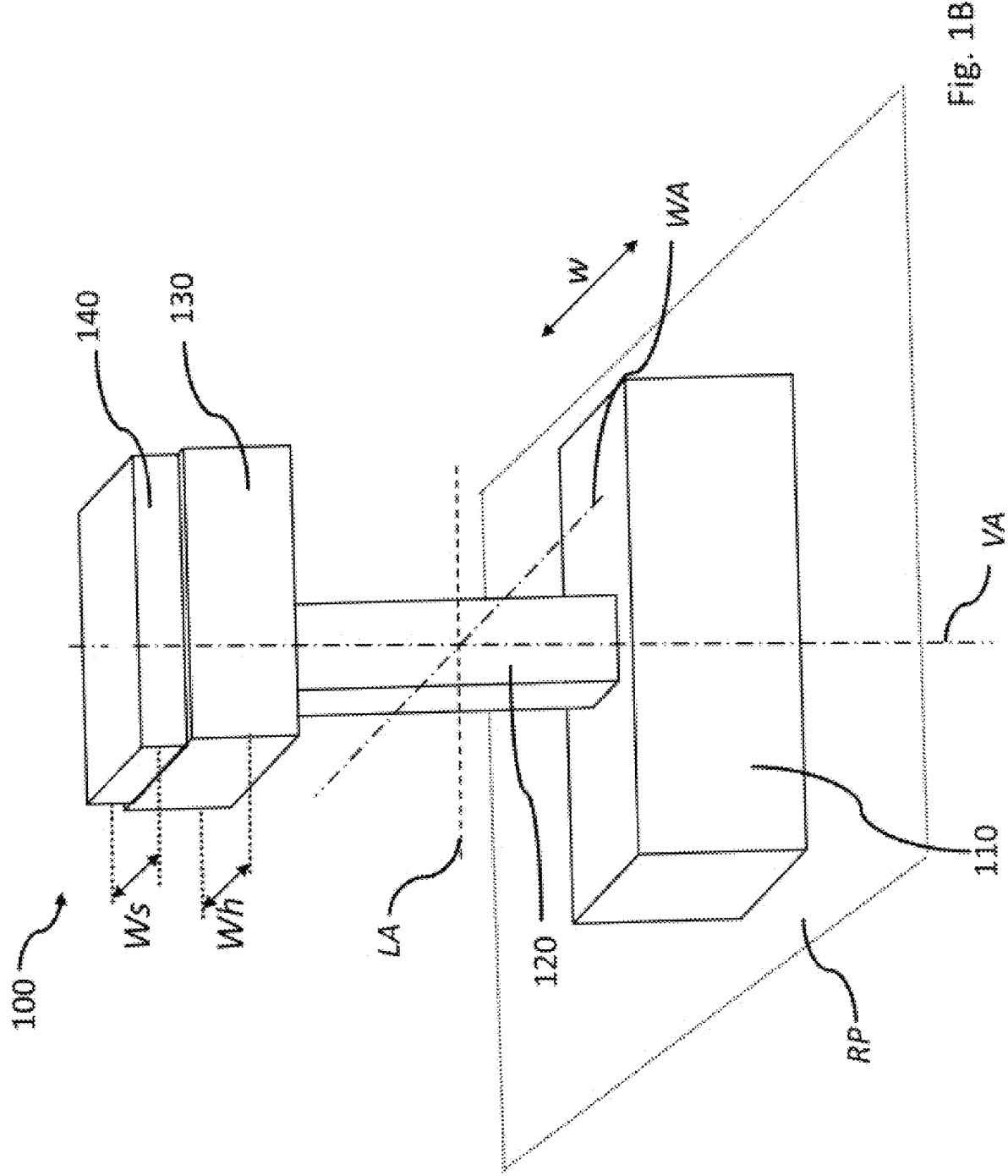

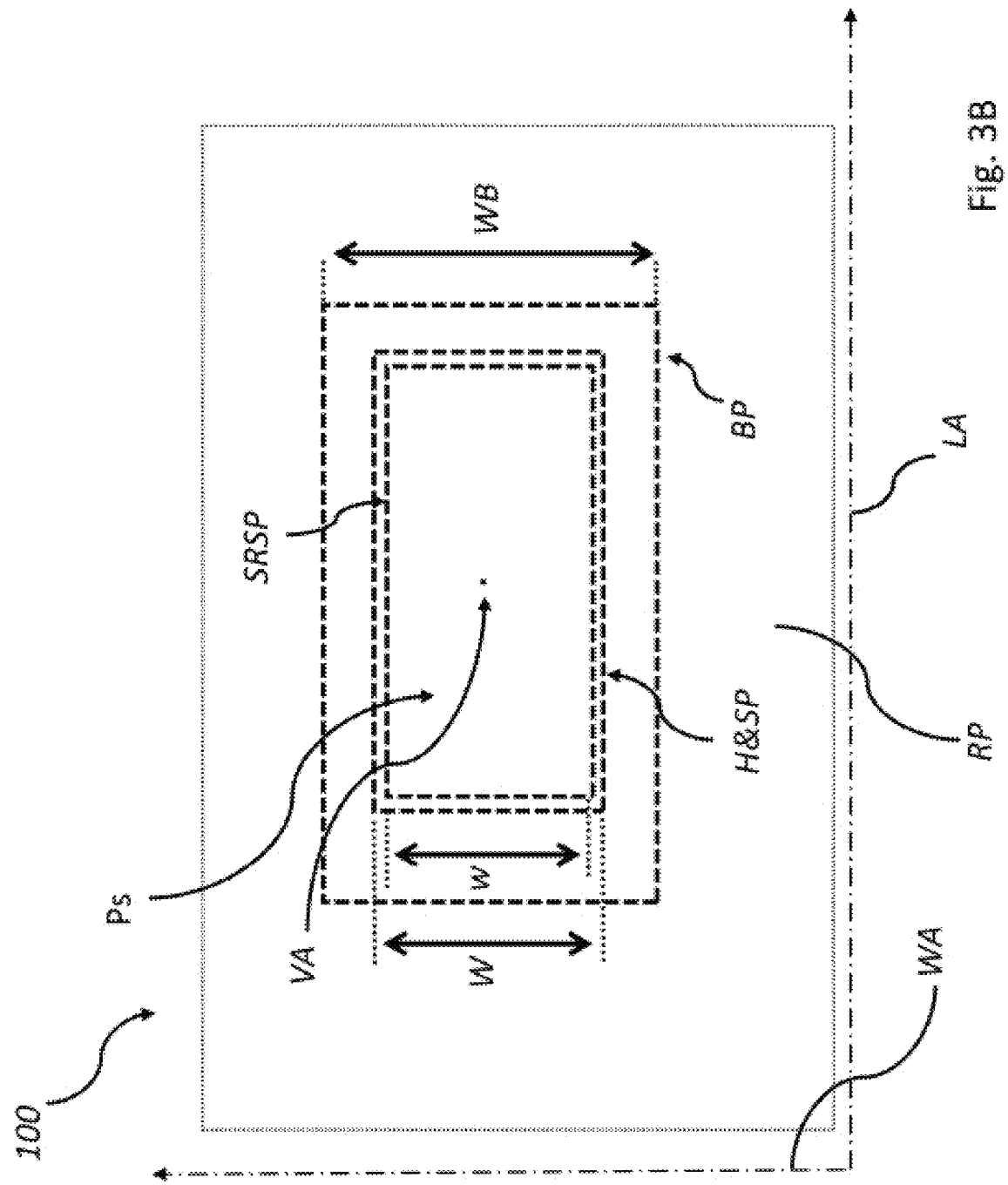

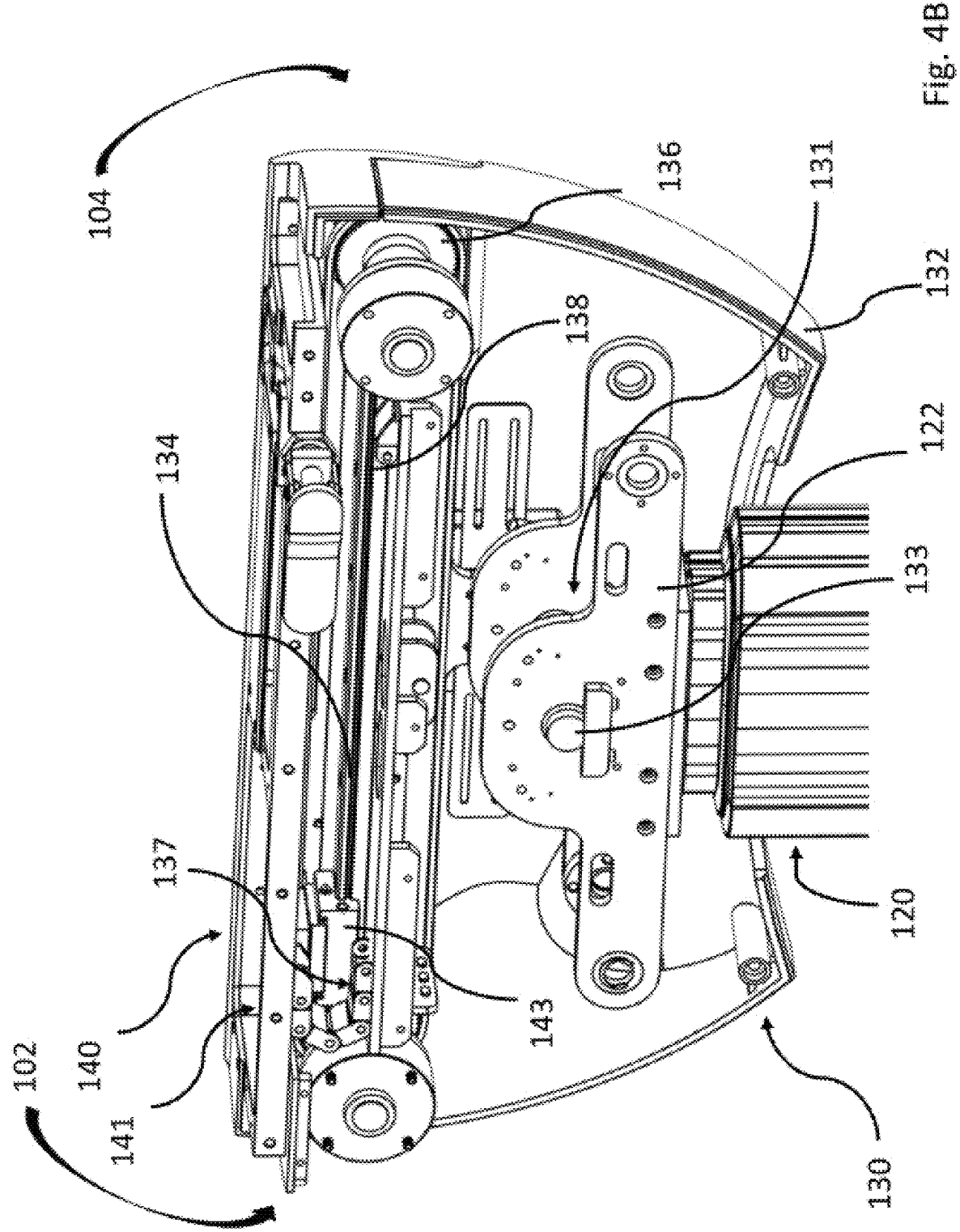

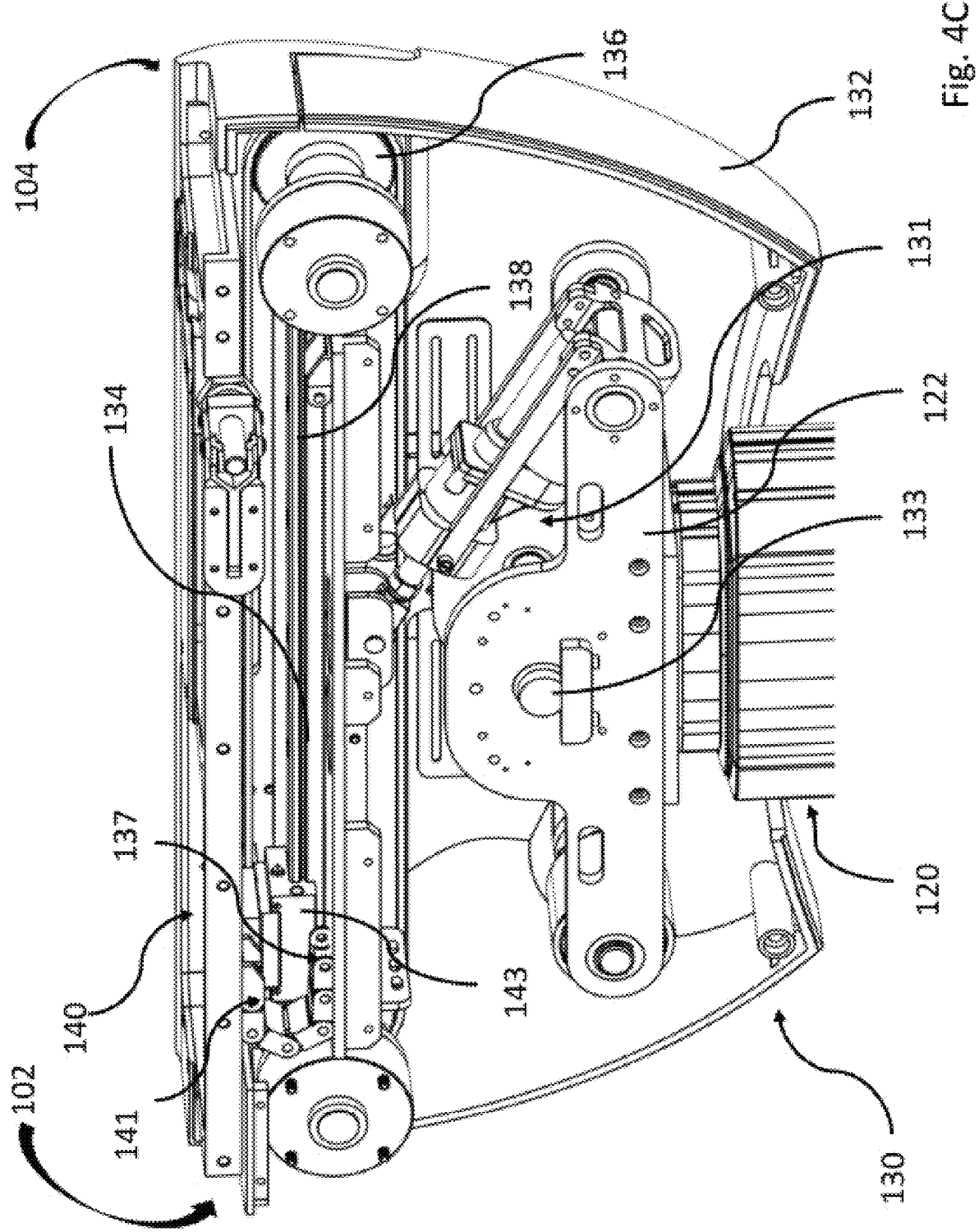

SURGICAL ROBOTIC POSITIONING CART

CROSS-REFERENCE TO RELATED APPLICATIONS

This patent application is a continuation-in-part of PCT Application No. PCT/IL2021/050188, filed on Feb. 17, 2021, which was published as International Publication No. WO2021/165963A1 on Aug. 26, 2021 and is incorporated herein by reference in its entirety. PCT/IL2021/050188 claims priority to Israel Patent Application No. IL272830, filed on Feb. 20, 2020.

TECHNOLOGICAL FIELD

The presently disclosed subject matter refers to the field of positioning carts for a surgical robotic tool mountable thereto, enabling a user to position such tool so as to manipulate therewith as desired immediately prior to a surgical procedure, more specifically immediately prior to transvaginal surgery.

BACKGROUND

More particularly, the presently disclosed subject matter refers to a positioning device for detachably attaching thereto a surgical robotic tool of the kind disclosed in U.S. Pat. No. 10,463,438, intended mainly for transvaginal procedures. In U.S. Pat. No. 10,463,438, this tool is disclosed as being mountable to a support arm configured for being fixed to a fixed element in a surgery room while providing the surgical robotic tool with a number of degrees of freedom.

There also exist surgical robots having a base body and one or more surgical arms integrally mounted to the body and manipulatable thereby, the base body having a plurality of additional functionalities typical for robots such as the 'Sehance'® which is manufactured by 'TransEnterix' or the 'Flex® Robotic System', which is manufactured by 'Medrobotics Corp.'.

SUMMARY

According to one aspect of the presently disclosed subject matter, there is provided a mobile surgical positioning cart configured for supporting a surgical device e.g. via a component of a surgical robotic device, so as to allow the surgical device to be linearly advanced at a selected angle and/or height into a body of a patient. The surgical positioning cart can have a proximal side, a distal side configured to face a surgical entry site of a patient and being substantially opposite to the proximal side, a central vertical axis disposed between the two sides, a longitudinal axis passing through the two sides and crossing the vertical axis, a width axis perpendicular to the longitudinal axis and the vertical axis, the longitudinal and width axes defining a horizontal reference plane.

The surgical positioning cart comprises a base, a neck, a head and a slider. More particularly, the base can be movable at least along the horizontal reference plane. The head can be tiltable/pivotable relative to the horizontal plane to define therewith different inclination angles at least in a plane comprising the vertical and the longitudinal axes. The slider can be configured to fixedly receive at least a portion of the robotic device thereon and be mounted to the head so as to be tilt/pivot therewith and be movable relative thereto at least along the longitudinal axis. The neck connecting between the base and the head (pivotally mounted thereto), can have an adjustable height defined by a length of the neck in the vertical direction.

The surgical robotic device has a length l and a width w essentially smaller than the length l, such that a projection of the head with the slider on the horizontal reference plane has a width W along the width axis, wherein a ratio w:W can be less than 1:2. More particularly, the ratio w:W can be less than 1:1.8, more particularly, less than 1:1.7, more particularly, less than 1:1.6 and more particularly between 1:1.5-1:1.6. In some examples, the ratio w:W can be 1:1.57. The ratio w:W can be any one of the following ranges 1:1.2-1:2, 1:1.4-1:1.8, 1:1.4-1:1.6, 1:1.5-1:1.6.

In some embodiments in which the surgical robotic device is fixedly received and/or mounted on the slider, w can also be a projection of the surgical robotic device on the horizontal reference plane, along the width axis. In this case, the surgical robotic device can have a number of motors arranged longitudinally therein, and the width w can be defined by a number of motors and their size in a plan view of the surgical robotic device, e.g. along the width axis.

Additionally or alternatively, the ratio of the width w of the surgical robotic device to the width Wh of the head, can be in the range of 1:1-1.2, wherein Wh is the width along the width axis of a projection of the head on the horizontal reference plane. For example, the width W of the projection of the head with the slider on the horizontal reference plane along the width axis of the cart can be smaller than 26 cm.

A projection of the neck on the horizontal reference plane can be disposed within the boundaries of a projection of the head on the horizontal reference plane at least in the width direction.

When the width of the head differs from the width of the slider, the projection of the one of them that is narrower, on the horizontal reference plane, can be within the boundaries of the projection of the other one that is wider along the width axis.

The slider can be mounted to the head so as to be slidable along the longitudinal axis. The slider can be movable between an extreme proximal position and an extreme distal position.

The head can have a longitudinal extension L1, which can extend along the longitudinal axis, and the slider can have a longitudinal extension L2, which can extend along at least a majority of longitudinal extension L1, for e.g., when the slider is positioned at the extreme proximal position. When the slider is positioned at the extreme distal position, at least a majority of the slider, e.g., along its the longitudinal extension L2, can distally protrudes from the head.

The surgical positioning cart can further comprise one or more controllers, which can be configured to control one or more of the following: the adjustment of the length of the neck, tilting/pivoting of the head, or the linear movement of the slider. The one or more controllers can be positioned at an extreme proximal end of the slider. More particularly, the one or more controllers can be positioned at an extreme proximal end of the cart. For example, one controller can be positioned at an extreme proximal end of a handle of the cart. In another example, a controller can be spaced from a proximal edge of the cart in the proximal direction. In some embodiments, the controller can operate the cart remotely, e.g., via any means of communication such as a cable or wireless transmission.

The base can have a base projection onto the horizontal reference plane with a distal base extremity at a distance D1 from the vertical axis. The head can have a head projection onto the horizontal reference plane with a distal head extremity at a distance D2 from the vertical axis. The neck can have a neck projection onto the horizontal reference plane with a distal neck extremity at a distance D3 from the vertical axis. Optionally, distance D1 can be greater than or equal to D2 and D3.

In one embodiment, an area of a projection of the cart on the reference plane, when the slider is in the extreme proximal position, e.g. in a compact configuration, can be smaller than 0.28 m².

The neck can have an oval shape such that a longitudinal extension L3 of the neck, extends along the longitudinal axis of the cart. The neck can be a telescopic pole, e.g. a telescopic oval pole.

The surgical positioning cart can further comprise a tilt adjusting mechanism including a tilt adjusting actuator, which can be configured to adjust the inclination angles of the head. The inclination angles of the head can be within the range of ±30 degrees with respect to the horizontal reference plane.

The slider can further be configured to lockingly engage a portion of the surgical robotic device. The slider can further be configured to allow movement of a moveable portion of the surgical robotic device relative to the portion of the device configured to lockingly engage the slider.

The slider of the surgical positioning cart can further comprise a connector mechanism configured to place and lock a portion of the surgical robotic device.

The slider of surgical positioning cart can further comprise at least two sockets disposed at a top surface of the slider, positioned at the distal and proximal ends of the slider, respectively. Each socket can be configured to receive therein a protruding element of the surgical robotic device and to enable the protruding elements to move linearly along the longitudinal axis with respect to the slider.

The projection of the base on the horizontal reference plane can have a width along the width axis, which is smaller than 45 cm. The projection of the head on the horizontal reference plane can be disposed within the boundaries of the projection of the base on the horizontal reference plane, at least in the width direction.

The base of the surgical positioning cart can have an interior configured to receive therein, at least one weight.

The surgical positioning cart can further comprise wheels associated with the base thereby allowing the base to be movable along the horizontal reference plane. The surgical positioning cart can be movable manually or electronically.

The surgical positioning cart can further comprise supporting legs, which can have a deployed configuration, for the purpose of improving the stability the cart or preventing the base from being movable at least along the horizontal reference plane. The supporting legs can further have a folded configuration, to allow the base to be moved at least along the horizontal reference plane.

The surgical positioning cart can further comprise a height adjusting actuator, which can be configured to manipulate the neck to adjust the height at which the head can be held above the base.

The surgical positioning cart can further comprise a slider actuator, which can be configured to set the movement of the slider.

The surgical positioning cart can further comprise electrical safety features, which can be configured to enable or disable any one or more of the height adjusting actuator, the tilt adjusting actuator, the sliding movement of the slider or the movement of the cart as a whole.

The slider of the surgical positioning cart can be movable relative to the head, at least along the longitudinal axis, e.g., via one or more rail(s) which can be positioned along the longitudinal axis of the head.

According to a further aspect of the presently disclosed subject matter, there is provided a method for aligning with a surgical entry site of a patient, a surgical positioning cart, e.g. as detailed above, supporting a surgical robotic device thereon, the method comprising: mounting the surgical robotic device on the slider, optionally, locking it thereon, moving the base at least along the horizontal reference plane, adjusting a height of the neck in the vertical direction, tilting/pivoting the head relative to the horizontal plane to define therewith different inclination angles at least in a plane comprising the vertical and the longitudinal axes, and sliding the slider along the longitudinal axis.

According to a further aspect of the presently disclosed subject matter there is provided a method of stabilizing and positioning a surgical robotic device with respect a surgical entry site of a patient, the method comprising: providing a cart, e.g. as detailed above, comprising a slider, a base, a head carrying the slider and a neck holding the head, e.g. as described above, mounting the surgical robotic device on the slider, and optionally, locking it thereon, moving the base at least along the horizontal reference plane to a position adjacent to a surgical entry site, adjusting a height of the neck, connecting between the base and the head, in the vertical direction, tilting/pivoting the head relative to a horizontal plane, and sliding the slider along the longitudinal axis.

According to another aspect of the presently disclosed subject matter, the surgical positioning cart supporting a surgical robotic device thereon according to any of the aspects of the presently disclosed subject matter described above, can be used to position and orient the surgical robotic device prior to vaginal approach surgery, an abdomen approach surgery or a head approach surgery. In a head approach surgery, the cart can be used to align the surgical robotic device relative to a treatment target location in a head of the patient, for example a port, an incision formed in the head of the patient, and/or a natural body orifice of the head, for example a mouth, in a way that optionally allows introduction of one or more elements of the device through the treatment target location in the head.

In all the above aspects, the surgical robotic device can be of the kind have robotic arms protruding from the remainder of the device, and the slider can be configured so that when the surgical device is mounted thereon, the robotic arms protrude distally from the remainder of the device and, optionally, from the slider.

The alignment of the surgical robotic device may be, at least partially, set by the positioning of the cart, which may be controlled by one or more actuators of the cart. For example, the method for alignment of the surgical robotic device may comprise adjusting position and/or orientation of the surgical robotic device, e.g., height and/or tilting angle, by using the cart.

In some embodiments of each of the above-described aspects of the presently disclosed subject matter, a controlled movement of each one of the elements of the cart can be performed independently from that of one or more of the other elements. For example, the controlled movement may comprise height and/or tilting angle adjustment of the head and slider, whereas the linear advancement of the slider can be performed separately form the head. The controlled movement may comprise a linear advancement of the slider towards a patient or a target area location in the patient. The linear advancement of the slider can be performed manually, which may allow for a fine-tuned and accurate movement of the slider towards target area.

According to some exemplary embodiments, at least some of the controller/s can comprise or be in the form of movement controllers, e.g. knobs and/or electronic switches, configured to control the activation of one or more actuators, for example electric motors, functionally connected to the elements of the cart, such as movable portions of the cart, e.g. the slider, the head, the neck or the base of the car. In some embodiments, the one or more movement controllers may control the activation of the one or more actuators according to values of a movement parameter indication, which may be stored in a memory of the cart, for example movement speed, movement time, movement acceleration, movement distance or any other movement-related parameter.

In some embodiments, the cart can comprise a user interface, which may be configured to generate a human detectable indications based on signals received from a movement sensor(s), e.g., to detect a location of the target area.

The cart can be used to place the surgical robotic device near a treatment target location of a patient, such as a natural orifice of the body, a surgical port, an incision, a target location on the external surface of the body or the skin of a patient. The cart can be configured to align the surgical robotic device or parts thereof, e.g., robotic arms of the surgical device, with the treatment target location. The slider configured for being advanced towards the target area location, can be configured for example to enable an insertion of one or more robotic arms of a surgical robotic device mounted thereon into the target area location or to bring the arms closer to the surgical target area location. For example, the slider can be configured to bring the surgical robotic device to a distance of less than 10 cm from the target area location.

According to some exemplary embodiments, the cart comprises at least one movement sensor electrically connected to the control circuitry configured to sense the position and/or orientation of the cart. The cart control circuitry can control the movement of the cart and/or one or more the elements thereof including the slider, such that they can be kept within a predestined range of values. For example, by activating or deactivating at least one actuator and/or motor configured to move the elements of the cart based on the measured position and/or orientation, the cart control circuitry can keep the movement of the cart or elements thereof within an predetermined range of values related to movement range, movement speed, acceleration and/or movement time. According to some exemplary embodiments, the control circuitry monitors the position and/or orientation of one or more of the components of the cart, e.g. slider, head, neck or base, during a surgical procedure, for example when robotic arms of the surgical robotic device are positioned inside the treatment target location and/or in contact with a body tissue. In some embodiments, if the monitored position and/or orientation changes, an alert signal or an indication can be generated.

According to some exemplary embodiments, the cart can comprise one or more locks for the fixation of the cart and/or of one or more of its components, particularly, the head and/or slider, in a desired position and/or orientation thereof. For example, the locks can be used for the fixation of the head and/or the slider at any desired height. The locks can be of the same or different kinds, e.g. they can be in the form of electromagnetic locks.

According to some exemplary embodiments, the tilt adjusting actuator can be functionally connected to a tilt adjuster user interface, which may be separate from or constitute a part of the user interface of the cart, and may be configured to control the activation of the tilt adjusting mechanism, e.g. by its being electrically connected to the interface. In some embodiments, the tilt adjuster user interface can comprise a switch configured to initiate the change of the tilting angle of the head and slider with respect to the reference plane, e.g. relative to a zero degrees state when the slider is parallel to the support surface. Optionally, the tilt adjuster user interface can allow automatically tilting of the head and slider to a zero degrees state. In some embodiments, the tilt adjuster user interface delivers a human detectable indication when reaching a zero degrees state, for example, by vibrating and/or sound.

According to some exemplary embodiments, the handle of the cart can comprise a tilting angle adjustment switch and a height adjusting switch close to each other, and optionally movable parallel to each other. In some embodiments, the handle comprises one or more slider advancing switches, for example two slider advancing switches. In some embodiments, a difference in the distance and/or angle between the positions of one or more slider advancing switches and other adjustment switches can reduce the risk of accidental activation of the one or more slider advancing switches when adjusting the height and/or tilting angle of the slider. Optionally, the handle can have a lower handle portion positioned lower than the at least one user interface. In some embodiments, the lower handle portion has a V-shape structure.

According to some exemplary embodiments, any of the movement adjusters (e.g. height adjuster or tilting adjuster) is functionally connected to a movement adjuster user interface. In some embodiments, the movement adjuster user interface allows to activate the movement adjuster manually and/or to control the movement of the slider. In some embodiments, a user may activate and/or deactivate the movement adjuster by activating one or more locks, for example electromagnetic locks, using the user interface.

In some embodiments, the cart can be part of a surgical unit, which may comprise the cart, the surgical robotic device and a control console configured to control the surgical robotic device. In some embodiments, once a position of the cart or any element thereof, e.g. the slider, is fixated, the control circuitry can deliver an indication to the control console indicating that the cart and the surgical robotic device are in place. According to some exemplary embodiments, the control console is configured to control at least some of the movements of the cart or any part thereof, e.g., by wireless and/or wired signal transmission.

According to some exemplary embodiments, the surgical robotic device can comprise a linear unit at the bottom portion of a surgical device, connectable to the slider, e.g. via the connector of the slider, which can be configured, when locked, to lock a portion of the surgical robotic device in place. The linear unit and the connector can comprise engageable mating elements, e.g. a male element of the linear unit lockingly receivable within a female element of the connector. In particular, the connector of the slider can comprise an opening which corresponds in shape and/or size to a protrusion formed in the linear unit of the surgical device.

According to some exemplary embodiments, arms, for example robotic arms, can be connected to the surgical robotic device e.g., after the robotic device is securely attached to the cart. Alternatively, a robotic device with one or more robotic arms e.g. 2, 4, 6, 8 or any intermediate, smaller or larger number of robotic arms, can be attached to the cart before mounting it to the slider. In some embodiments, the one or more robotic arms can be functionally connected to a motor unit of the surgical robotic device through one or more upper opening in the motor unit casing of the surgical robotic device. In some embodiments, the robotic arms are connected to the motor unit only after the linear unit is connected and locked to the slider of the cart.

In some embodiments, the controlling to the cart and/or elements thereof, can be performed remotely, such as remote-controlling of the height and/or tilt angle of the head, e.g., from the console or from a tablet. In some embodiments, the remote control can be connected wirelessly to the cart, and can be controlled from two spaced places, remote location and the user interface of the cart. In some embodiments, the controllers can enable fine tuning of the angle/height. Additionally, the controllers can enable automatically returning to "home" positioning and/or saving positioning of the last coordinates, in case the user wishes to repeat the positioning, and return it.

In the presently disclosed subject matter the term 'width' with respect to any physical device or a part thereof or a projection thereof on a plane, e.g. reference plane and/or a supporting surface, means its maximal width at least along the width axis.

The above general description has been provided so that the nature of the presently disclosed subject matter can be generally understood without being limited to specific embodiments and examples. A more specific description is provided in the Detailed Description whilst the following are non-limiting examples of different embodiments of the presently disclosed subject matter:

Embodiment 1: A surgical positioning cart configured to support a surgical robotic device thereon, the cart having a proximal side, a distal side configured to face a surgical entry site of a patient and being substantially opposite to the proximal side, a central vertical axis disposed between the two sides, a longitudinal axis passing through the two sides and crossing the vertical axis, a width axis perpendicular to the longitudinal axis and the vertical axes, the longitudinal and width axes defining a horizontal reference plane, the cart comprising:
 a base movable at least along the horizontal reference plane;
 a head pivotable relative to the horizontal plane to define therewith different inclination angles at least in a plane comprising the vertical and the longitudinal axes;
 a slider configured to fixedly receive at least a portion of the robotic device thereon and mounted to the head so as to be pivotable therewith and be movable relative thereto at least along the longitudinal axis; and
 a neck connecting between the base and the head pivotally mounted thereto, having an adjustable height defined by a length of the neck in the vertical direction.

Embodiment 2: The surgical positioning cart according to embodiment 1, wherein the surgical robotic device has a length l and a width w essentially smaller than the length l, such that a projection of the head with the slider on the horizontal reference plane has a width W along the width axis wherein a ratio w:W is less than 1:2.

Embodiment 3: The surgical positioning cart according to embodiment 2, wherein the surgical robotic device has a number of motors arranged longitudinally therein and the width w is defined by the number of motors and their size in a plan view of the surgical robotic device.

Embodiment 4: The surgical positioning cart according to any one of the preceding embodiments, wherein the slider is movable between an extreme proximal position and an extreme distal position.

Embodiment 5: The surgical positioning cart according to embodiment 4, wherein the head has a longitudinal extension L1 along the longitudinal axis, and the slider has a longitudinal extension L2 and it extends along at least a majority of the longitudinal extension L1, when the slider is positioned at the extreme proximal position.

Embodiment 6: The surgical positioning cart according to embodiment 5, when dependent directly or indirectly on embodiment 4, wherein when the slider is positioned at the extreme distal position at least a majority of thereof along the longitudinal extension L2 distally protrudes from the head.

Embodiment 7: The surgical positioning cart according to any one of the preceding embodiments, wherein the width of the projection of the head with the slider on the horizontal reference plane along the width axis of the cart is smaller than 26 cm.

Embodiment 8: The surgical positioning cart according to any one of the preceding embodiments, further comprising at least one controller configured to control at least one of the adjustment of the length of the neck, the pivoting of the head or the linear movement of the slider.

Embodiment 9: The surgical positioning cart according to embodiment 8, wherein the at least one controller is positioned at an extreme proximal end of the slider.

Embodiment 10: The surgical positing cart according to claim 8, wherein the at least one controller is positioned at an extreme proximal end of the cart.

Embodiment 11: The surgical positioning cart according to any one of the preceding embodiments, wherein when a width of the head differs from a width of the slider, the projection on the horizontal reference plane of the one of them that is narrower is within the boundaries of the projection on the plane of the other one that is wider along the width axis.

Embodiment 12: The surgical positioning cart according to any one of the preceding embodiments when dependent directly or indirectly on embodiment 2, wherein a projection of the head on the horizontal reference plane has a width W along the width axis such that a ratio w:W is in the range 1:1-1:2.

Embodiment 13: The surgical positioning cart according to any one of the preceding embodiments, wherein the base has a base projection onto the horizontal reference plane with a distal base extremity at a distance D1 from the vertical axis; the head has a head projection onto the horizontal reference plane with a distal head extremity at a distance D2 from the vertical axis; and the neck has a neck projection onto the horizontal reference plane with a distal neck extremity at a distance D3 from the vertical axis, such that distance D1 is greater than or equal to each one of D2 and D3.

Embodiment 14: The surgical positioning cart of any one of the preceding embodiments, wherein a projection of the neck on the horizontal reference plane is disposed within the boundaries of a projection of the head on the horizontal reference plane at least in the width direction.

Embodiment 15: The surgical positioning cart according to any one of the preceding embodiments, when dependent directly or indirectly on embodiment 4, wherein an area of a projection of the cart on the reference plane, when the slider is in the extreme proximal position, is smaller than 0.28 $m^2$.

Embodiment 16: The surgical positioning cart according to any one of the preceding embodiments, wherein the neck has an oval shape in its plan view, such that a longitudinal extension L3 of the neck extends along the longitudinal axis of the cart.

Embodiment 17: The surgical positioning cart according to any one of the preceding embodiments, wherein the head is pivotable in a plane comprising the longitudinal and width axes.

Embodiment 18: The surgical positioning cart according to any one of the preceding embodiments, wherein the slider is further configured to lockingly engage a portion of the surgical robotic device.

Embodiment 19: The surgical positioning cart according to any one of the preceding embodiments, wherein the slider is further configured to allow movement of a moveable portion of the surgical robotic device relative to the portion of the device configured to lockingly engage the slider.

Embodiment 20: The surgical positioning cart according to any one of the preceding embodiments, wherein the slider further comprises a connector mechanism configured to place and lock a portion of the surgical robotic device.

Embodiment 21: The surgical positioning cart according to any one of the preceding embodiments, wherein the slider further comprising at least two sockets disposed at a top surface of the slider positioned at the distal and proximal ends of the slider, respectively, each socket is configured to receive therein a protruding element of the surgical robotic device and to enable the protruding elements to move linearly along the longitudinal axis with respect to the slider.

Embodiment 22: The surgical positioning cart of any one of the preceding embodiments when dependent directly or indirectly on embodiment 13, wherein the projection of the base on the horizontal reference plane has a width along the width axis, which is smaller than 45 cm.

Embodiment 23: The surgical positioning cart of any one of the preceding embodiments when dependent directly or indirectly on embodiment 13, wherein the projection of the head on the horizontal reference plane is disposed within the boundaries of the projection of the base on the horizontal reference plane at least in the width direction.

Embodiment 24: The surgical positioning cart of any one of the preceding embodiments, wherein the base has an interior configured to receive therein at least one weight.

Embodiment 25: The surgical positioning cart of any one of the preceding embodiments, further comprising wheels associated with the base and allowing the base to be movable along the horizontal reference plane.

Embodiment 26: The surgical positioning cart according to any one of the preceding embodiments, further comprising supporting legs having a deployed configuration configured to improve the stability the cart and a folded configuration, such that when the supporting legs are in the deployed configuration, they prevent the base from being movable at least along the horizontal reference plane.

Embodiment 27: The surgical positioning cart according to embodiment 26, wherein when the supporting legs are in their folded configuration, the base is movable at least along the horizontal reference plane.

Embodiment 28: The surgical positioning cart according to any one of the preceding embodiments, wherein the inclination angles are within the range ±30 degrees with respect to the horizontal reference plane.

Embodiment 29: The surgical positioning cart according to any one of the preceding embodiments, further comprising a height adjusting actuator configured to manipulate the neck to adjust the height at which the head is held above the base.

Embodiment 30: The surgical positioning cart according to any one of the preceding embodiments, further comprising a tilt adjusting actuator configured to adjust the inclination angles of the head.

Embodiment 31: The surgical positioning cart according to any one of the preceding embodiments, further comprising a slider actuator configured to set the movement of the slider.

Embodiment 32: The surgical positioning cart according to any one of the preceding embodiments, wherein the cart is movable manually.

Embodiment 33: The surgical positioning car according to embodiments 30 to 32, further comprising an electrical safety features configured to enable or disable the operation of each of the height adjusting actuator, the tilt adjusting actuator, the sliding movement of the slider or the movement of the cart as a whole.

Embodiment 34: The surgical positioning cart according to any one of the preceding embodiments, wherein the slider is movable relative to the head at least along the longitudinal axis via one or more rail(s) extending along the longitudinal axis of the head.

Embodiment 35: The surgical positioning cart according to any one of the preceding embodiments, wherein the neck is a telescopic pole.

Embodiment 36: The surgical positioning cart according to any one of the preceding embodiments, when dependent directly or indirectly on embodiment 2, wherein the ratio w:W is less than 1:1.8, optionally less than 1:1.7, optionally less than 1:1.6.

Embodiment 37: The surgical positioning cart according to any one of the preceding embodiments, when depending on embodiment 2, wherein the ratio w:W is in one of the following ranges 1:1.2-1:2, 1:1.4-1:1.8, 1:1.4-1:1.6, 1:1.5-1:1.6.

Embodiment 38: The surgical positioning cart according to any one of the preceding embodiments, when dependent directly or indirectly on embodiment 2, wherein the ratio w:W is 1:1.57.

Embodiment 39: The surgical positing cart according to embodiment 8, wherein the at least one controller is spaced from a proximal edge of the cart in the proximal direction.

Embodiment 40: A method for aligning a surgical positioning cart supporting a surgical robotic device thereon with a surgical entry site of a patient, the cart having a proximal side, a distal side configured to face the surgical entry site and being substantially opposite to the proximal side, a central vertical axis disposed between the two sides, a longitudinal axis passing through the two sides and crossing the vertical axis, a width axis perpendicular to the longitudinal axis and the vertical axes, the longitudinal and width axes defining a horizontal reference plane, the cart comprising a base, a neck, a head and a slider mounted to the head, the neck connecting between the base and the head, the method comprising:
  mounting the surgical robotic device on the slider, and optionally, locking it thereon;
  moving the base at least along the horizontal reference plane;
  adjusting a height of the neck in the vertical direction;
  pivoting the head relative to the horizontal plane to define therewith different inclination angles at least in a plane comprising the vertical and the longitudinal axes; and
  sliding the slider along the longitudinal axis.

Embodiment 41: A method of stabilizing and positioning a surgical robotic device with a surgical entry site of a patient, the method comprising:

providing a cart comprising a slider, a base, a head carrying the slider and a neck holding the head;

mounting the surgical robotic device on the slider, and optionally, locking it thereon;

moving the base at least along the horizontal reference plane to a position adjacent to a surgical entry site;

adjusting a height of the neck, connecting between the base and the head, in the vertical direction;

pivoting the head relative to a horizontal plane; and sliding the slider along the longitudinal axis.

Embodiment 42: A method of embodiment 40 or 41, wherein the surgical positioning cart is according to any one of embodiments 1 to 39.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 1B is a perspective view of the surgical positioning cart shown in FIG. 1A;

FIG. 3B schematically illustrates projections of the base, the head and the slider of the cart shown in FIGS. 1A and 1B on a horizontal plane;

FIG. 4B illustrates one example of an interior of a head of the cart shown in FIG. 4A, according to an embodiment of the presently disclosed subject matter;

FIG. 4C illustrates one example of an interior of a head of the cart shown in FIG. 4A, according to an embodiment of the presently disclosed subject matter;

DETAILED DESCRIPTION OF EMBODIMENTS

Described below is a mobile surgical positioning cart configured to support a surgical device/tool, such as a surgical robotic device, according to the presently disclosed subject matter so as to allow the surgical device to be linearly advanced at a selected angle and/or height into a body of a patient. For example, the positioning cart can be positioned such that the surgical device is aligned with a selected treatment target location of the patient or near the selected target location, by being movable along a horizontal plane.

According to the presently disclosed subject matter, the cart has a compact design and/or a relatively small footprint, at least of its component holding the surgical robotic device, at least along its width axis, thereby enabling a user, e.g. a doctor, a nurse and/or technician, to bring the system close to the treatment target location, without blocking a field of view (FOV) of the user.

The treatment target location can be any one of: a body entry site, for example a port formed in the patient, an incision in the patient, an anatomical orifice of the patient or any other opening in a body of the patient. Alternatively, or additionally, the target location comprises a treatment target site located on an external surface of the body, for example on the skin of the body. According to the presently disclosed subject matter, the cart is shaped and sized to allow easy vaginal access to a treatment target location, for example by placing the cart between spread legs of a patient.

Figure 1A:
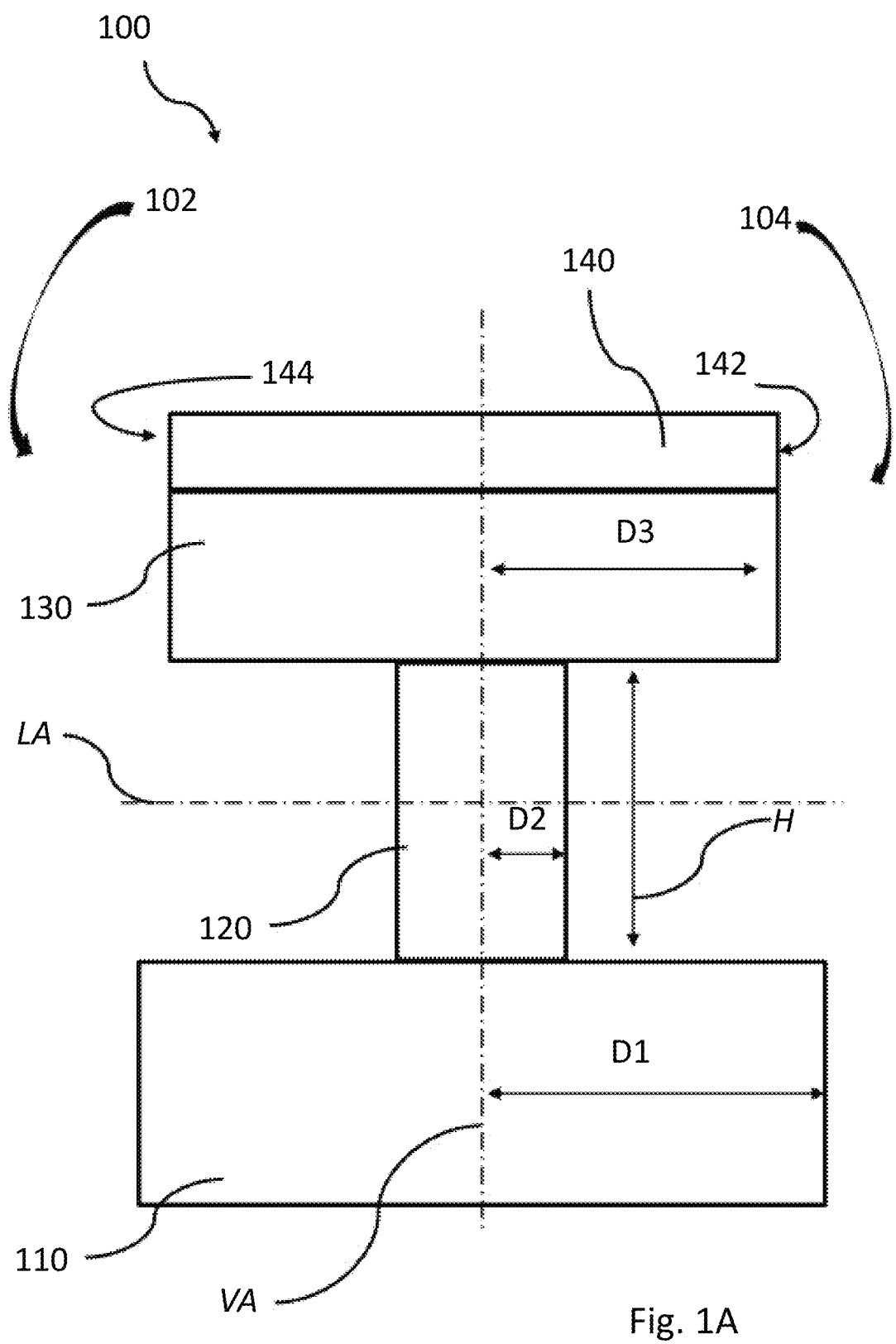
FIG. 1A is a side view of a schematically illustrated surgical positioning cart, according to an embodiment of the presently disclosed subject matter, the cart being in its initial state.

Reference is now made to FIGS. 1A and 1B schematically illustrating a side view and a perspective view, respectively, of the mobilized surgical positioning cart 100, according to an embodiment of the presently disclosed subject matter, configured to support a surgical robotic device (not shown) to be positioned thereon, which has a length l and a width w essentially smaller than the length l, e.g. the ratio between the length l and the width w is at least 3.5:1. Such system, for example, can have a number of motors disposed in at least two rows along the length of the system and their size define the width w of the system in its plan view. One example of such system is disclosed in U.S. Pat. No. 10,463,438 of the Applicant.

The cart 100 has a proximal side 102, a distal side 104 being substantially opposite to the proximal side 102 and configured to face a patient, e.g. a surgical entry site of the patient, a central vertical axis VA disposed between the two sides, a longitudinal axis LA passing through the two sides and crossing the vertical axis VA, a width axis WA perpendicular to the longitudinal axis LA and the vertical axes VA, the longitudinal LA and width axes WA defining a horizontal reference plane RP (shown in FIG. 1B). The longitudinal axis LA, the width axis WA and the horizontal reference plane RP can be considered as being located anywhere along the vertical axis VA and their different locations can be shown in the drawings depending on the location of a component described relative thereto.

The cart 100 comprises a base 110, a neck 120, a head 130 and a slider 140.

Figure 4A:
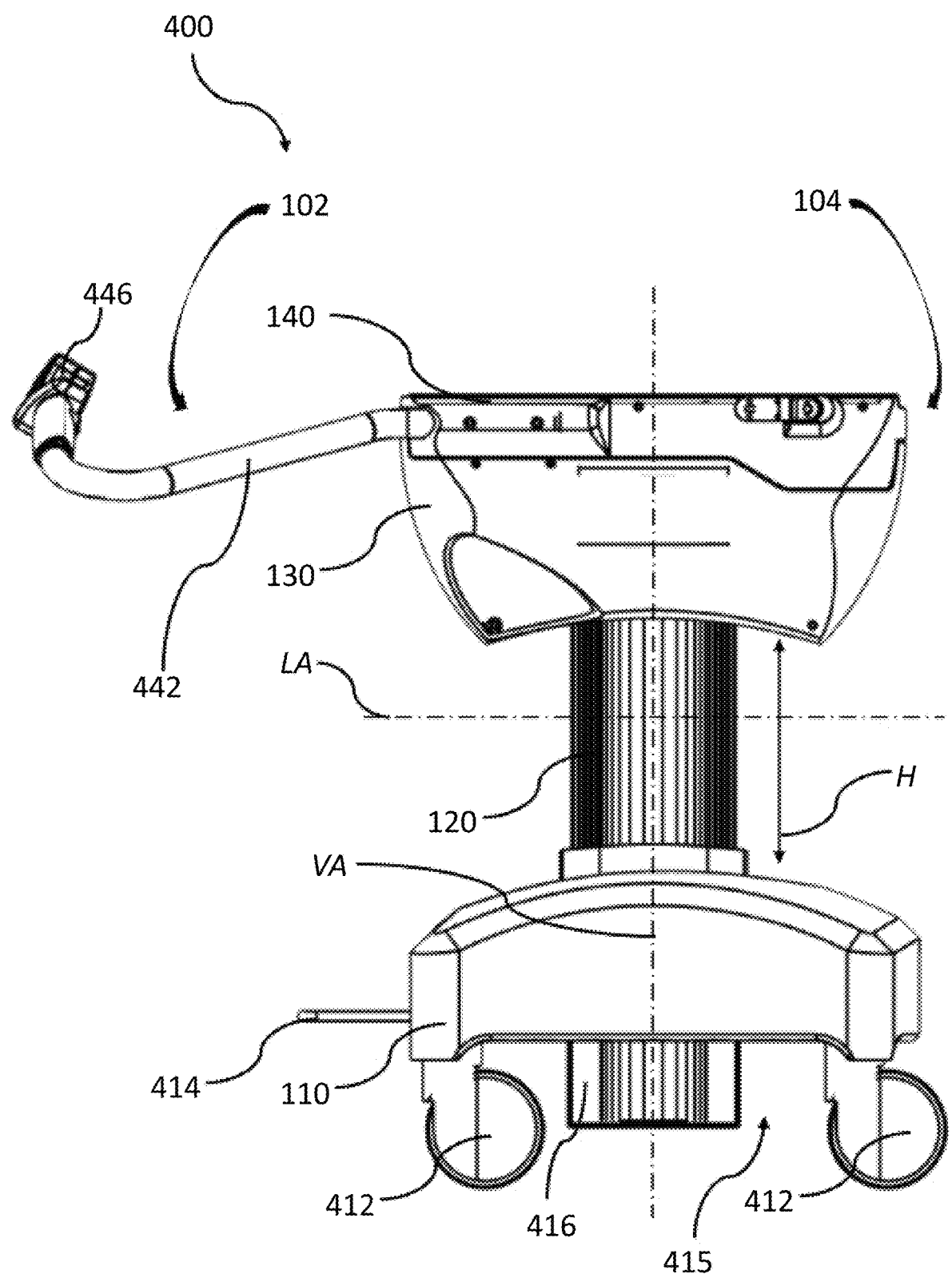
FIG. 4A is a side view of a mobilized cart, according to another embodiment of the presently disclosed subject matter.
Figure 5A:
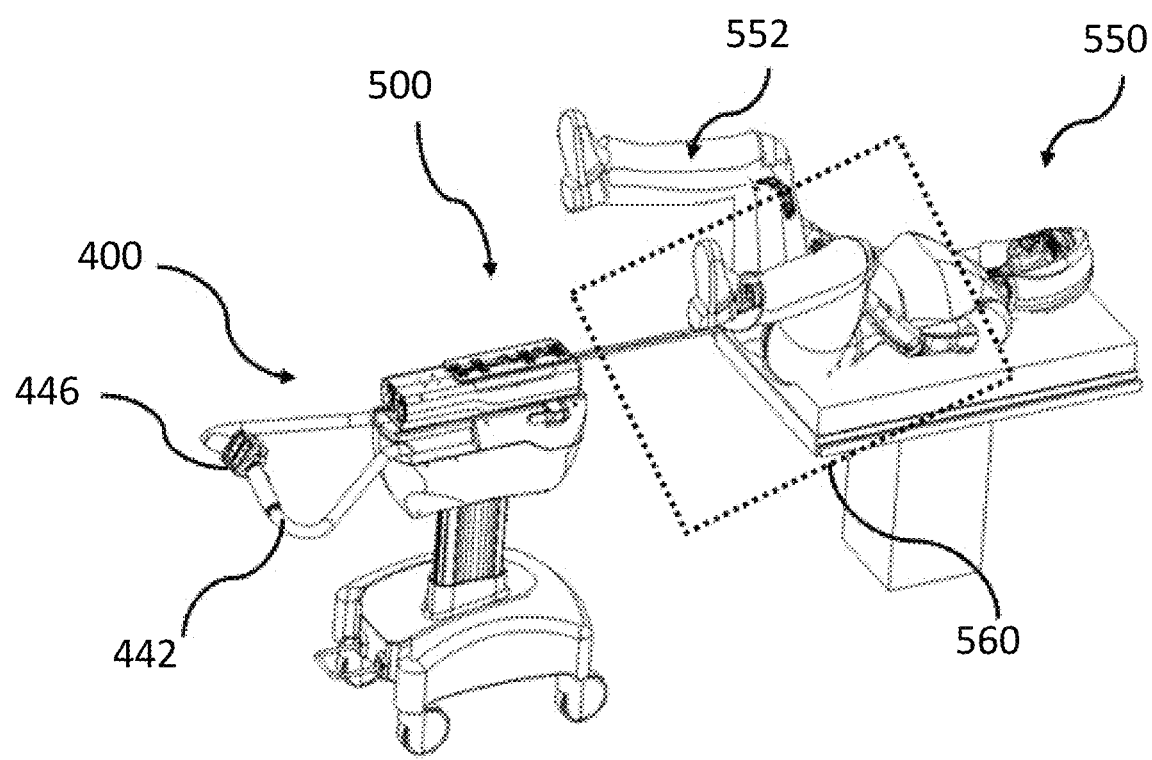
FIGS. 5A and 5B illustrate the cart shown in FIG. 4A with a surgical robotic device mounted thereto for operation at a target area location, with its slider being in an initial position and in an extended position, respectively.
Figure 5B:
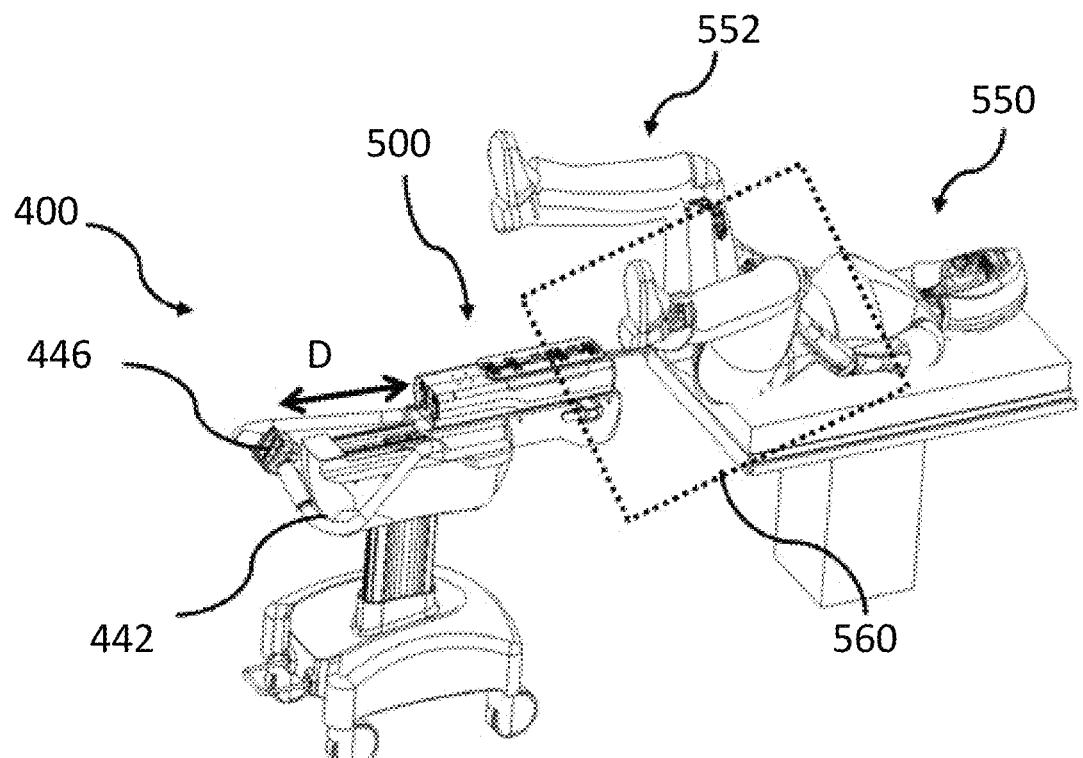

According to the embodiments shown, inter alia, in FIGS. 4A, 5A, 5B, 6, 7A, 7B, and 8, and described further hereinbelow, the base 110 includes wheels for moving the cart at least in a longitudinal direction. The neck 120 has a height that can be extended and shortened, e.g., to adjust the height of a surgical robotic device borne by the cart 100 to a desirable height. The head 130 provides a stable platform for supporting a surgical robotic device and has a generally horizontal, or even substantially horizontal, top surface. The head 130 is configured to pivot on a pitch axis relative to the neck 120, e.g., to change an orientation of the surgical robotic device when present. An upper portion of the head 130, e.g., an uppermost portion exposed to user access from the top, can include a slider 140, which comprises a slidable docking interface for a surgical robotic device. The head 130 can also provide for example, an optimized location for having attached thereto a handle for the cart, and for attaching (either directly to the head 120 or to the handle attached thereto) a user control panel displaced proximally from the patient end of the cart and from the surgical robotic system supported thereby, if present. Exemplary arrangements of a handle and a control panel are shown in FIGS. 4A, 5A, and 5B, while their absence in other figures is for merely purposes of simplification and does not imply the absence of such arrangements in an actual cart.

The slider 140 is configured to slide longitudinally relative to the cart, where extending the slider 140 can be helpful in bringing a surgical arm of the surgical robotic device to a target location, e.g., at an access point for a surgical operation. The surgical robotic device is detachably attachable to the slider 140 from the top of the slider, and if desired can be attached to the slider 140 for performing a surgical operation, and detached therefrom after an operation for maintenance and storage. As will be made clear in the drawings, the slider 140 is constructed such that it pivots together with the head 130, and the surgical robotic device is attachable (dockable) to the slider 140 such that when the surgical robotic device is present, i.e., docked to the slider 140, the surgical robotic device pivots together with the slider 140 and the head 130. When the surgical robotic device is present, i.e., docked to the slider 140, it also moves longitudinally together with the longitudinal sliding of the slider 140 relative to the head 130 and to the rest of the cart 100. Inter alia, this allows for the surgical robotic device, and especially one or more surgical arms seated proximally in an arm-receiving section of the surgical robotic device, to displace distally and closer to, and/or through, an access point for a surgical operation, without moving the entire cart closer. The slider 140 is configured to receive a surgical robotic device at its upwards-facing docking interface so that the surgical robotic device can move together with the slider in any of at least three displacements: vertical, longitudinal, and in a pitch axis.

As shown, e.g., in FIGS. 4A, 5A, 5B, 6, 7A, 7B, and 8, the cart is designed such that the weight of the surgical robotic device is supported entirely by the slider 140 on which it sits, i.e., to which it is docked, on the uppermost portion of the cart 100. In addition to advantages described above with respect to ease of positioning the surgical robotic device by changing the position and/or orientation of the slider (and surgical device, when present) together with the head of the cart, this arrangement, inter alia, allows for user access to simple and convenient replacement of the surgical robotic device and/or of surgical arms seated proximally in arm-receiving portions of the surgical robotic device. In a first example, it can become desirable during a surgical operation to replace a surgical arm without changing the position of the surgical robotic device and/or of the cart supporting the device. In a second example, it can become necessary during a surgical operation to replace the entire surgical robotic device, e.g., because of a malfunction or for any other reason, and again without withdrawing the cart from the patient. In both example, the replacement would be unnecessarily complicated if the surgical robotic device were not attached/docked to the slider on the top surface of the head of the cart.

Still referring to FIGS. 1A and 1B, the base 110 is configured to provide structural support for other components of the cart 100 and to be movable therewith along a support surface such as a floor of the operating room being parallel thereto. For the purpose of the present description, the support surface will be considered as being parallel to or being defined by the horizontal reference plane RP. The base 110 can have a projection on the horizontal reference plane RP larger than that of the other components of the cart 100 and/or can have an interior configured to receive therein and/or thereon at least one weight so as to ensure the stability of the cart.

Figure 1C:
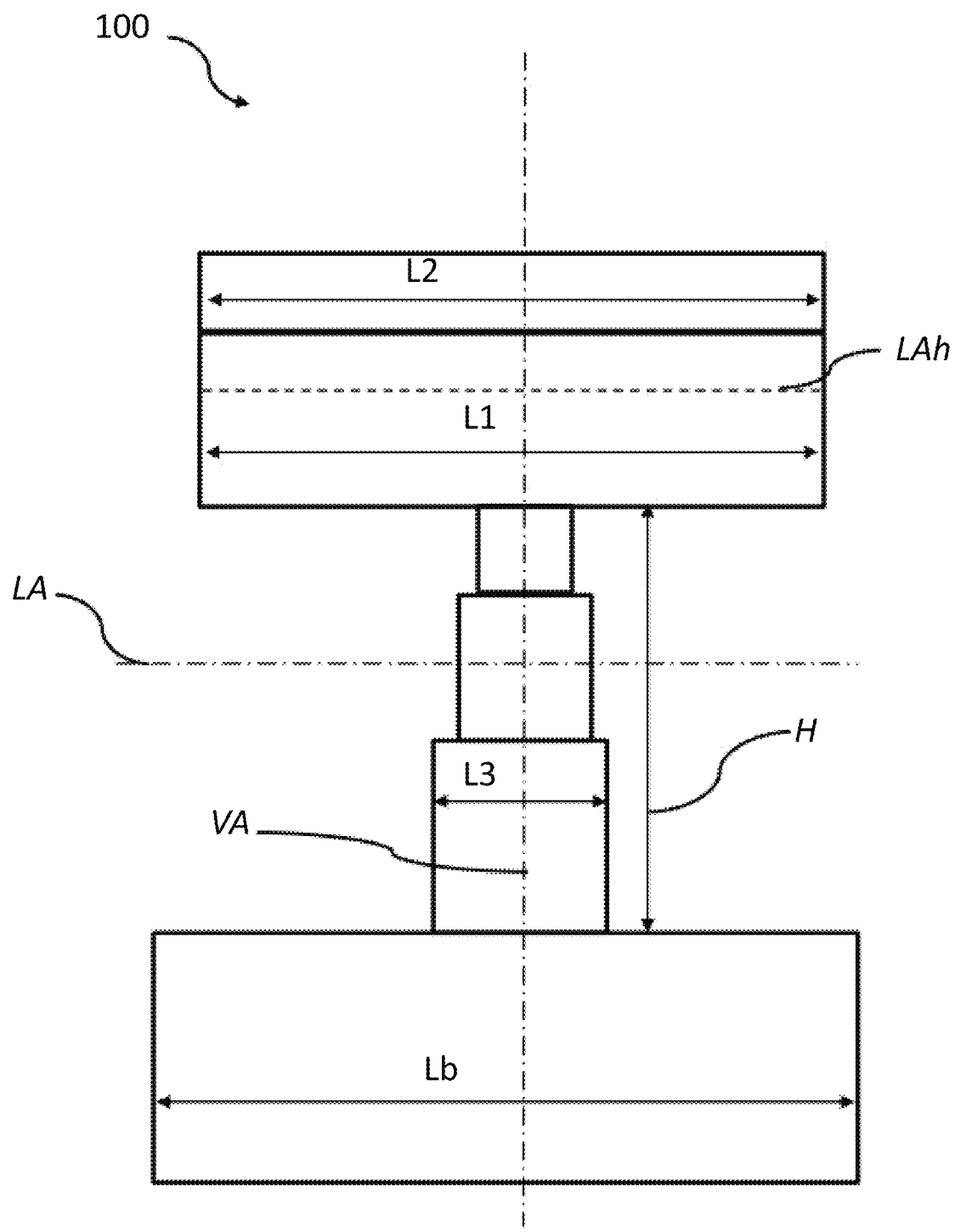
FIG. 1C is a side view of the surgical positioning cart shown in FIGS. 1A and 1B, with the neck being extended.

The neck 120 is mounted to the base 110 and its height H is adjustable along the central vertical axis VA, as illustrated in FIG. 1C. For example, the neck 120 can be in the form of a telescopic pole and either the neck 120 or the base 110 can comprise an actuator configured to manipulate the height H of the neck 120. The height H of the neck can vary between 34 cm in a compact configuration and 115 cm in the extended configuration, therefore setting the variation in the total height of the cart from 0.86 meters in the compact configuration and up to 1.7 meters in the extended configuration. The neck 120 can have an oval shape such that the longitudinal extension L3 of the neck is oriented along the longitudinal axes.

Figure 1D:
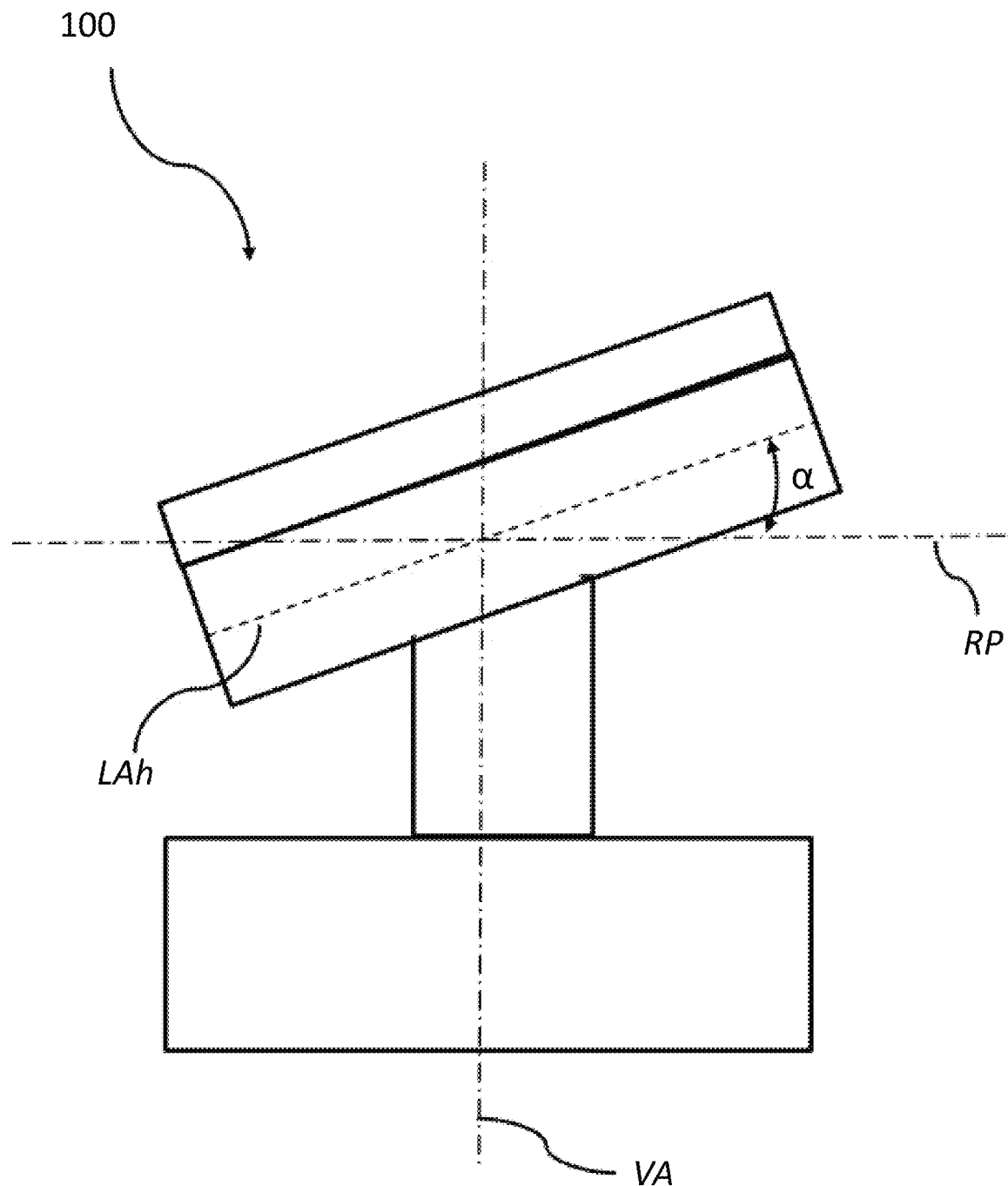
FIG. 1D is a side view of the surgical positioning cart shown in FIGS. 1A and 1B, with the head being tilted relative to its base.

The head 130 is pivotably mounted to the neck 120 allowing the head to be inclined at different inclination angles relative to the horizontal plane RP. The head 130 has a longitudinal extension L1 along a longitudinal axis LAh and the head 130 can be pivotable about its width axis WA so as that the longitudinal axis LAh forms a varying angle α with the reference plane RP in a plane comprising the vertical axis VA and the longitudinal axes LA, as illustrated in FIG. 1D. The tilting angle α can very within the range ±30 degrees with respect to the reference plane RP when this plane passes through the center of the head 130 it is disposed at the intersection of its longitudinal and width axes. This range can be narrower, e.g. it can be ±25 degrees, ±15 degrees, more particularly, ±5 degrees for preforming a vaginal procedure. Optionally, the head 130 can be also pivotable about its longitudinal axis LAh and/or about the vertical axis VA.

Figure 2:
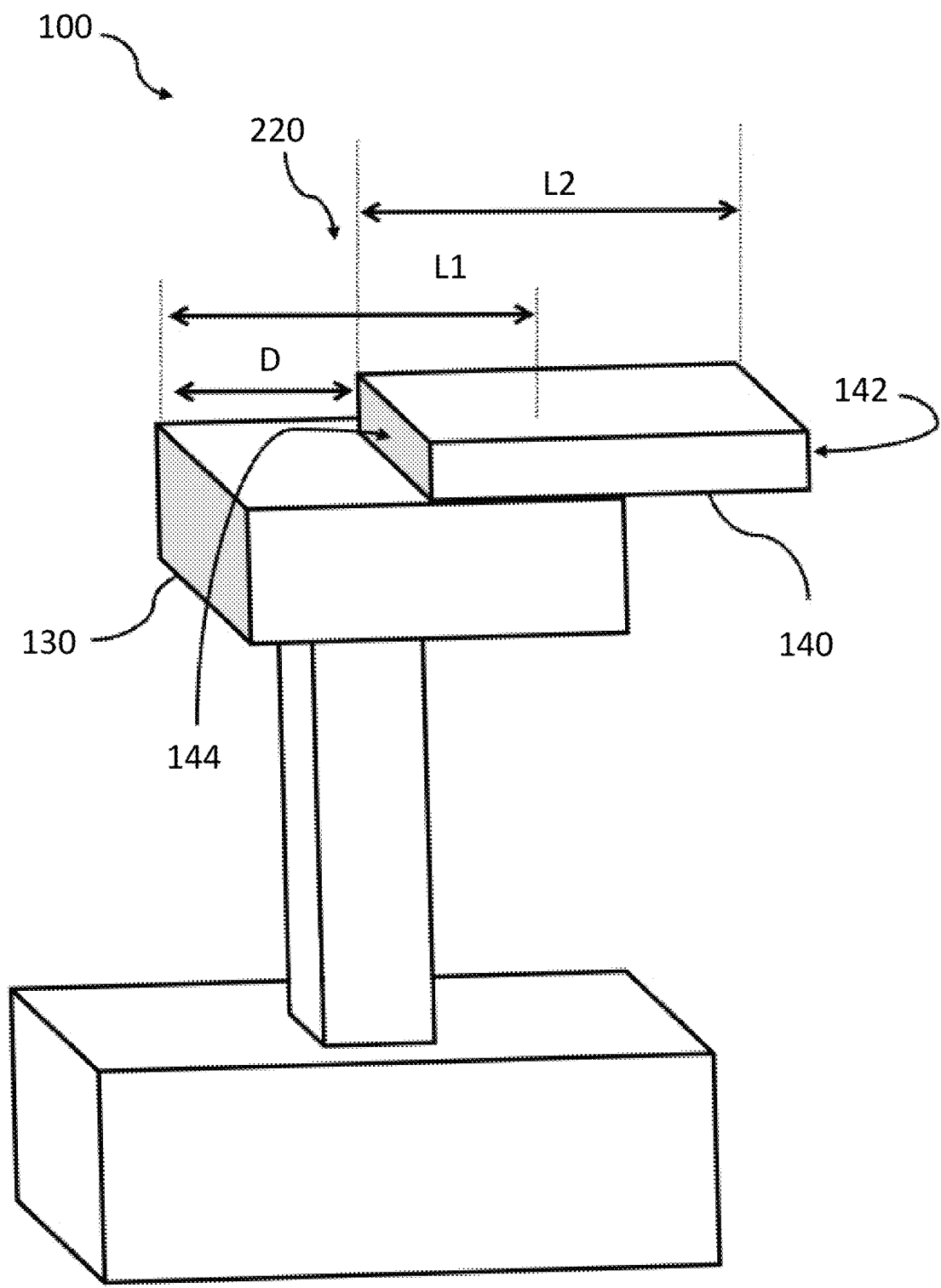
FIG. 2 is a perspective view of the surgical positioning cart shown in FIGS. 1A and 1B, with the slider being displaced.

The slider 140 is slidably mounted to the head 130 so as to be movable along the longitudinal axis LAh between the slider's extreme proximal position shown in FIGS. 1A to 1D and its extreme distal position designated as 220 in FIG. 2. When positioned at the extreme proximal position, the slider 140, having a longitudinal extension L2, extends along at least a majority of a longitudinal extension L1 of the head 130, i.e. its distal end 142 does not protrude or does not protrude essentially from the head 130 in the distal direction. In the extreme distal position 220, the distal end 142 of the slider protrudes essentially from the head 130 in the distal direction to bring the surgical device closer to the selected treatment target location. Thus, when positioned at the extreme distal position 220, the distal end 142 of the slider is moved, with respect to the extreme proximal position, by a distance D which is at least 30% of the slider's length, more particularly, at least 40%, and more particularly, at least 50%, for example 58%, with the length of the slider being 54 cm, the distance D can be as long as 31 cm.

Figure 3A:
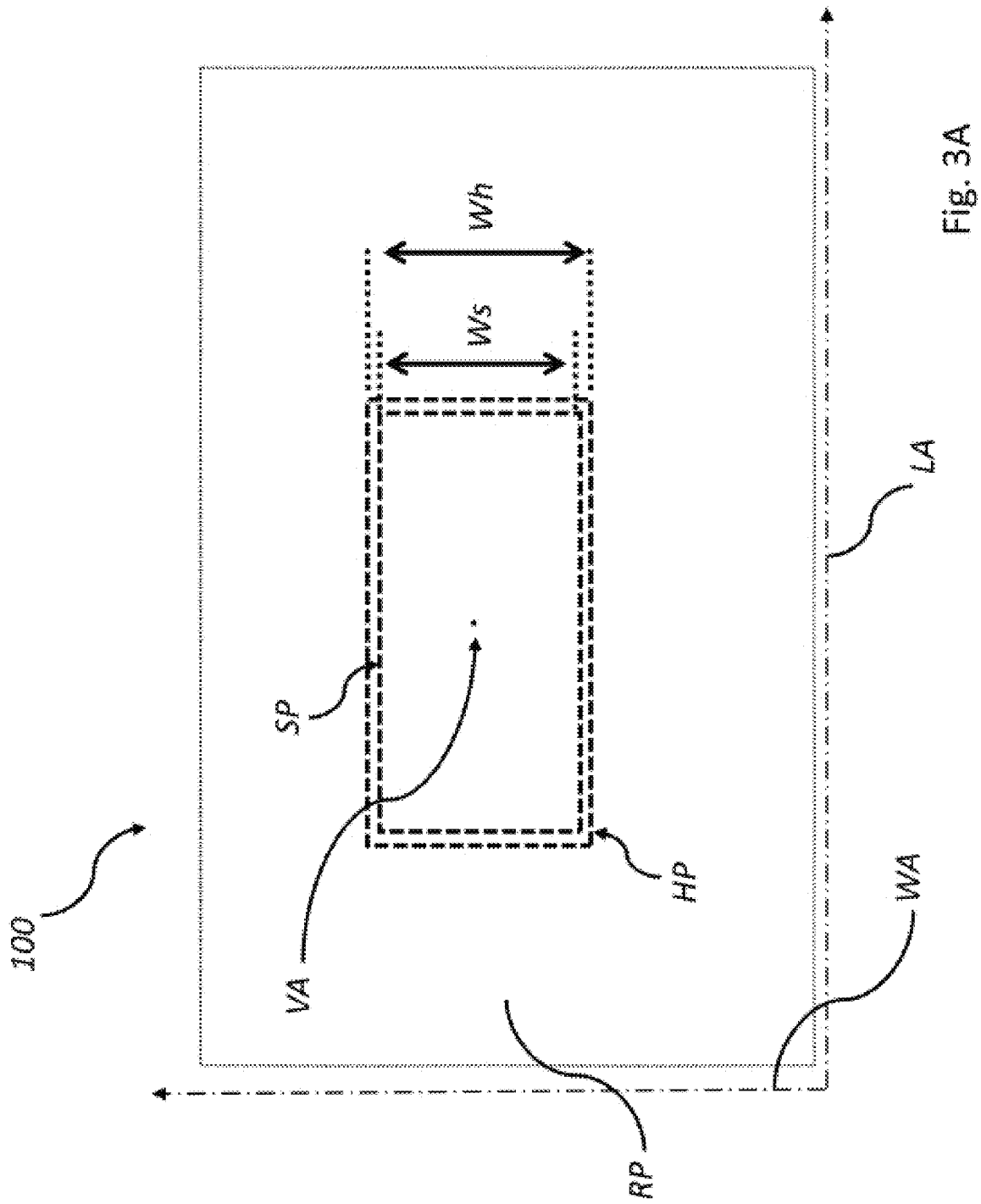
FIG. 3A schematically illustrates projections of the head and the slider of the cart shown in FIGS. 1A and 1B, on a horizontal plane.
Figure 3C:
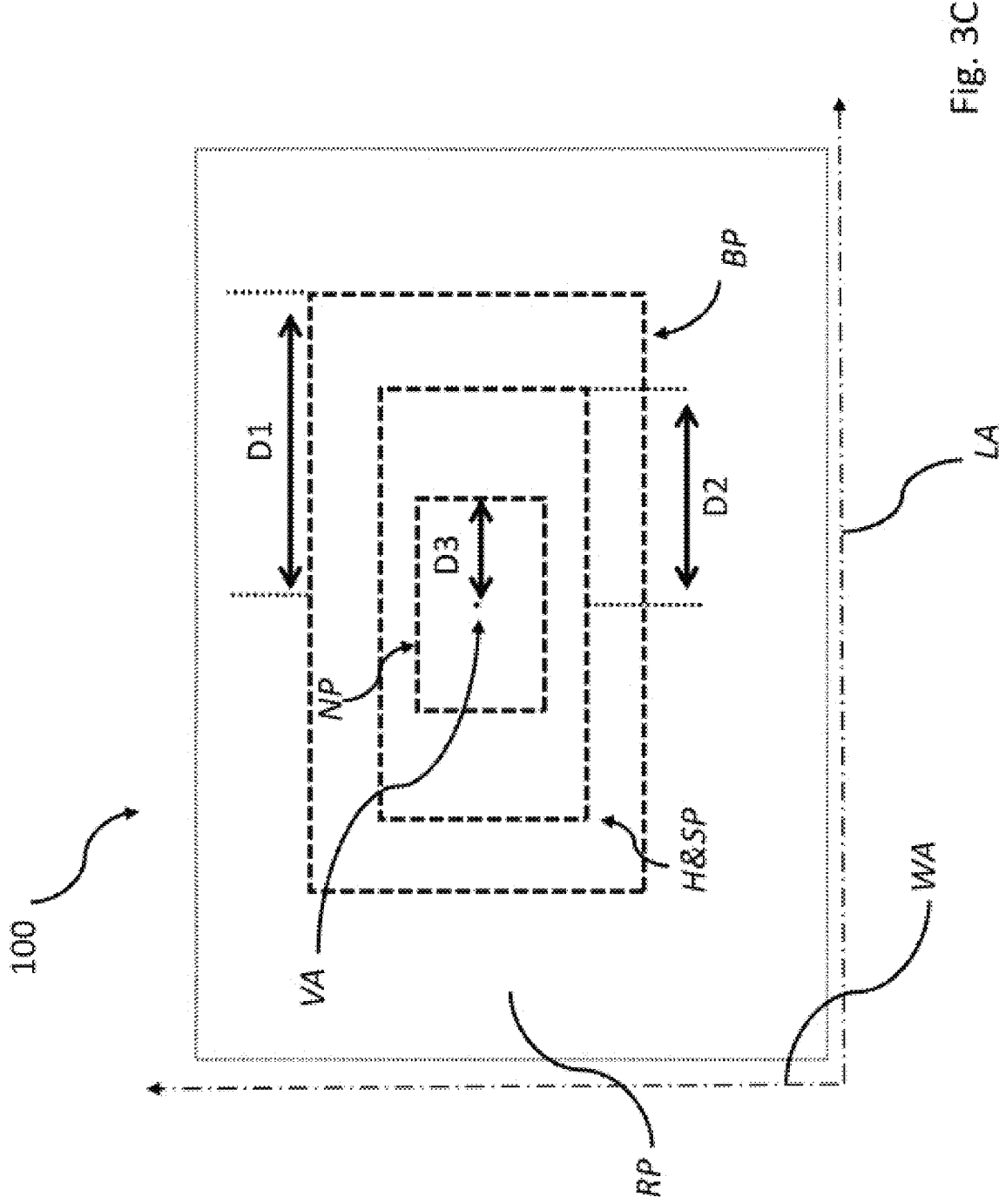
FIG. 3C schematically illustrates projections of the base, the neck, the head and the slider of the cart shown in FIGS. 1A and 1B on a horizontal plane.

Reference is now made to FIG. 3A, which is a plan view of the horizontal reference plane RP with projections of the head 130 and the slider 140 thereon, designated as HP and SP respectively. FIG. 3B is a plan view of the horizontal reference plane RP with projections of the head and slider with the surgical robotic device thereon, designated as H&SP and SRSP respectively. In the present example, the width of the projection of the slider Ws can be smaller, equal or greater, than the width of the projection of the head Wh, along the width axis WA. However, in any case, the projection of the one of them that is narrower is within the boundaries of the projection of the other one that is wider, at least along the width axis WA. It should be noted that the width of the projection of the head with the slider H&SP on the horizontal reference plane RP is smaller than 26 cm, for example, 22 cm. As illustrated in FIG. 3C, a projection of the neck NP on the horizontal reference plane RP in the cart 100 of the present example has an area which is essentially smaller than that of the head 130 and is disposed within the boundaries of the projection of the head HP, at least in the width direction, e.g. along the width axis WA. As seen in FIG. 3C, the head and slider projection H&SP on the horizontal reference plane RP is disposed within the boundaries of the base projection BP, at least along the width axis WA; and the neck projection NP on the horizontal reference plane RP is disposed within the boundaries of the head and slider projection H&SP on the horizontal reference plane RP, at least in the width direction, e.g., in the width axis WA.

When the cart 100 of the present example is configured to be used with the surgical robotic device of the kind mentioned above and having the width w, the width of the head 130 and of the slider 140 can exceed or be substantially equal to the width w of the surgical robotic device. Accordingly, in the present example, the width W of the projection of the head 130 with the slider 140 on the horizontal reference plane RP exceeds the width w of the robotic device. For example, a ratio w:W can be less than 1:2, more particularly, less than 1:1.8, more particularly, less than 1:1.7, more particularly, less than 1:1.6 and still more particularly it can be between 1:1.5-1:1.6. One specific example of the ratio w:W is 1:1.57.

More particularly, when the cart 100 of the present example is intended to support the surgical robotic device described in U.S. Pat. No. 10,463,438 of the Applicant, in this specific application the shape and size of the cart 100 can be such that the width W of the head 130 and slider 140 do not exceed a pre-determined dimension, e.g. 26 cm, enabling the cart 100, and more particularly, its head 130 with the slider 140 to be positioned between spread legs of any expected patient to allow direct and uninterrupted access to a vaginal target location in the patient body.

The width of the base 110 does not necessarily have to be as narrow as that of the head 130 with the slider 140 and it should be sufficient to provide the head mounted to the neck with stable and reliable support. Thus, in the cart 100 of the present example the projection on the horizontal reference plane RP of the base 110 has a width WB along the width axis WA, which is equal to or greater than the width W of the head with the slider. On the other hand, at least for the above mentioned specific application the base 110 can still be relatively narrow, e.g. to have the width WB smaller than 45 cm.

In general, the length and the weight of the base 110 should be selected so as to allow the base to maintain the stable and reliable support of the head 130 with the slider 140, even when the slider 140 is in its extended state 220 as shown in FIG. 2. Thus, in the cart 100 of the present example, the base 110 can have such a length Lb along the longitudinal axis LA, as to be at least not shorter than the head 130.

The elements of the cart 100 can have different longitudinal dimensions, i.e. different distances between their distal and proximal extremities and, more particularly between their distal extremities and the central vertical axis VA of the cart. In the present example, the base 110 has a base projection BP onto the horizontal reference plane RP with a distal base extremity at a distance D1 from the vertical axis VA, the head 130 along with the slider 140, in the extreme proximal position, have a head and slider projection H&SP onto the horizontal reference plane RP with a distal head and slider extremity at a distance D2 from the vertical axis VA; the neck 120 has a neck projection NP onto the horizontal reference plane RP with a distal neck extremity at a distance D3 from the vertical axis VA. In this embodiment, the distance D1 is greater than or equal to each one of the distances D2 and/or D3. Additionally, the distal extremity of the head 130 protrudes distally farther away from the distal extremity of the neck 120, i.e. D2 is greater than or equal to D3. Since the distal extremity of the neck 120 can be shorter than each one of the distal extremity of the head 130 and the base 110 in the distal direction, i.e., D2 can be smaller than D1 and D3, i.e., the cart 100 can have a general 'C' shape in the side view.

The general 'C' shape of cart 100 as well as the described above proportions between dimensions of different elements thereof can enable the user to position the cart 100 at a close proximity to the treatment target location with the cart being very compact. For example, the base 110 can fit under the patient resetting surface, such as a bed or a chair, while the head 130, slider 140 and the surgical robotic device can be positioned above the patient resetting surface, and therefore at a close proximity to the treatment target location. For example, at least for the above mentioned specific application, the above lengths can be in the following ranges: the length Lb of the base 110 is between 52 cm and 62 cm, and D1 is between 28 cm and 34 cm, the longitudinal extension of the neck L3 is between 14 and 20 cm and D3 is between 7 and 10 cm, the longitudinal extension of the head L1 is between 52 and 60 cm and similarly the longitudinal extension of the slider L2 is between 52 and 60 cm and D2 is between 24 and 29 cm.

With the dimensions described above, the cart 100 can be extremely compact and occupy a relatively small total area footprint, i.e., the area of its projection on the reference plane RP can be smaller than 0.28 m$^2$.

FIG. 4A illustrates another example of a mobilized cart, according to the presently disclosed subject matter. In this example, the cart designated as 400 has proximal and distal sides 102 and 104, respectively, as well as all the components described above with respect to the cart 100, including a base 110, a neck 120, a head 130 having a housing 132 with an interior space and a slider 140, all moveable and having parameters as described above. In view of this, below are described mainly those features of the cart 400 that are not present or not described in detail in the description of the cart 100.

In addition, the cart 400 has wheels 412 mounted to the base 110 so as to enable the cart 400 to be roll-able along a support surface, for example on the floor. The wheels have such dimensions and are so mounted to the base 110 as to protrude downwardly therefrom thereby forming a space 415 under the base, i.e. between the base and a horizontal plane passing through lowermost points of the wheels.

Although not illustrated, the base 110 can further comprise one or more wheel brakes configured to prevent the wheels 412 from rolling, thereby providing stability for the cart 400 after positioning it at its designated position, e.g. to prevent a continuous movement of the cart 400 on the surface.

The wheel brakes can be activated and/or deactivated manually and/or electronically by a hand switch and/or a leg switch. In the example shown in FIGS. 4, the cart 400 has a foot lever 414 for this purpose.

The cart 400 further comprises a height adjusting actuator 416 to actuate the extension of the neck 120 along the vertical axis VA of the cart. The actuator 416 is mounted to the base 110, thereby serving as a weight at the base 110, thus lowering the center gravity of the cart 400 and increasing its overall stability and/or balance. The height adjusting actuator 416 can comprise a drive in the form of e.g. an electric motor, a pneumatic actuator and/or a hydraulic actuator. In the present example, the actuator 416 is mounted to the base 110 so as to protrude downwardly therefrom into the space 415, thereby further facilitating the compactness of the cart 400.

The cart 400 further comprises a tilting mechanism (not seen in FIG. 4A) disposed within the interior of the housing of the head 130 and configured to tilt/pivot the head so as to change an angle between the longitudinal axis of the head LAh and the horizontal reference plane RP. This mechanism can comprise with a tilt adjusting actuator operable manually or it can comprise a drive in the form of e.g. an electric motor, a pneumatic actuator and/or a hydraulic actuator. The head 130 can be mounted to the neck 120 by means of such tilting mechanism.

The cart further comprises an elongated sliding assembly also disposed within the interior of the housing of the head 130 and configured to move the slider 140 along the longitudinal axis of the cart. This elongated sliding assembly can be operable manually or it can comprise a drive in the form of e.g. an electric motor, a pneumatic actuator and/or a hydraulic actuator.

The sliding assembly can be connected on the one hand to the tilting mechanism and on the other hand to the housing so as to allow its being tilted together with the housing relative to the tilting mechanism.

The cart 400 further comprises a handle assembly protruding proximally relative to all other components of the cart 400 and mounted so as to allow a user to move the cart 400 along the support surface. In the present example, the handle assembly designated as 442 protrudes proximally relative to all other components of the cart 400 and is mounted to the slider 140 at its proximal end 144 so as, on the one hand, to allow a user to move the cart 400 along the support surface when the slider 140 is fixed in place, and on the other hand, to move the slider 140 along the longitudinal axis LA of the cart when the cart 400 is fixed in place.

The cart 400 can comprise at least one controller 446 configured to control, or at least enable or disable, the extension of the neck 120 and/or the tilting/pivoting of the head 130 and/or the movement of the slider 140. In the present example, the controller can be configured to control the height adjusting actuator 416, the tilt adjusting actuator, the brakes of wheels 412 or the locking mechanism of the slider. Optionally, the controller can control the movement of wheels 412 too. The controller can be mounted anywhere in the cart, e.g. the at least one controller 446 can be positioned at an extreme proximal end of the cart 400, or operate the cart 400 remotely, e.g. via any means of communication such as a cable or wireless transmissions.

The cart 400 can comprise various means of user interface options connected to the controller 446, such as mechanic knobs and/or electronic switches, to enable the user to operate the controller. The user interface can be a remote one or rather it can be provided on the cart at its proximal side or at least closer to the proximate side than to the distal side of the cart. The controller and the associated user interface can be in the form of an assembly, which can be mounted, for example, on the handle assembly 442, the head 130 or the slider 140 (close to its proximal end). In the present example, the controller designated as 446 is mounted to the handle assembly at the most proximal area thereof.

In order to prevent unintentional movement of any one of the elements of the cart 400, such as wheels 412, neck 120, head 130 and/or slider 140, some safety mechanisms are installed in the controller 446 such as, for example, cause the user to continuously engage certain element/s of the user interface of the controller 446 to enable the movement of the relevant component of the cart. For example, in order to move the slider 140 the user can be required to press one or two sliding knob while physically pushing and/or pulling the slider 140, i.e. only then can the slider 140 slide distally or proximally. Other safety mechanisms can further include engaging two user interface elements at the same time, requiring the use of an electronic key, such as an employee badge, 'dead man's switch', emergency stop button for cutting the power supply in general or for specific elements of the cart and/or any combination thereof.

To provide appropriate control of the cart 400 and to minimize human errors the elements of the user interface configured to cause the controller to operate the tilting adjuster and the height adjusting actuatorheitilt can be spaced apart from one another and/or be positioned on opposite locations of the user interface.

Although not illustrated, to further increase the safety of the patient the cart 400 can optionally comprise a control circuitry, electrically connected to a memory, and configured to restrict the tilting angle of the head 130 with the slider 140 according to the indicated stored memory, for example to prevent tilting in an angle larger than a selected angle value (similar for the height adjustment). Additionally, the cart 400 can also comprise an orientation sensor, which can be connected to the controller. The orientation sensor can comprise a gyroscope and/or an accelerometer. The orientation sensor can be configured to sense changes in orientation of the head 130 and/or slider 140. For example, the orientation sensor can sense changes in rotation, such as tilting angle, of the head 130, slider 140 and/or cart 400 as a whole, with respect to each of the elements comprising the cart 400 and/or relative to a vertical axis VA and/or horizontal reference plane RP.

In order to avoid malfunctions due to power short circuits and to improve mobility options within the operating room with minimal footprint interference, the cart 400 can comprise an internal power source, such as a rechargeable battery. In other embodiments, the crat can further comprise a power distribution circuitry, electrically connected to an external power source.

Although not illustrated, the cart 400 can further comprise supporting legs having a folded state allowing the cart to be moved by means of its wheels, and a deployed state which they can take to prevent the cart from being moved thus allowing to improve the stability of the cart when the surgical robotic device is in operation.

FIG. 4B illustrates an example of the interior of the head 130 of the cart 400, having a housing 132, the tilting mechanism generally designated as 131, and the elongated sliding assembly generally designated as 141 with the slider 140 mounted thereto.

The tilting mechanism 131 can be mounted to a top portion of the neck 120 so as to pivot the head 130 about a pivoting mounting point 133. The tilting mechanism can comprise a tilt adjusting actuator (not shown) e.g. in the form of a piston movable or extendable at least partially along the longitudinal axis LAh of the head, to pivot the head 130 around pivotally mounting point 133. Alternatively, the tilt adjusting actuator can be configured to pivot itself around the pivotally mounting point 133 and be fixedly connected to the head 130. In any case the general design of the tilting mechanism is such that it does not have a large footprint, at least in the width direction, thereby enabling the shape and size of the head 130 to have dimensions as described above, e.g. to have a maximum combined width W of 26 cm.

When the tilt adjusting actuator (not illustrated in FIG. 4B) is in the form of a piston, the latter can be disposed between the distal side of the top portion of the neck 122 and a bottom portion of the sliding assembly 141, thereby having, at least a majority, of its footprint extending along the longitudinal axis LAh. Accordingly, the head 130 can further comprises a spring which is designed to apply a resisting force to the tilt adjusting actuator, thereby facilitating smother tilting motion of the head 130, upon adjustment of its inclination angle. FIG. 4C illustrates one example of a head, in which such structure is implemented.

The elongated sliding assembly 131 can comprise one or more slider supporting elements movable with the slider and a slider locking mechanism enabling locking the slider 140 or the slider supporting element/s in any desired fixed position relative to the sliding actuator. In the present example shown in FIG. 4B or 4C, the sliding assembly comprises a runner 143 movable along one or more rails (not seen) mounted to and fixedly held within the housing 132 and the slider locking mechanism 137 is configured to prevent the runner from moving along the rail/s. To this end, the slider locking mechanism of the present example comprises straps 138 extending between rollers 136 fixedly connected to the runner 143 and movable therewith, thus rotating the rollers 136, and means disabling the rotation of the rollers, thereby preventing the linear movement of slider 140. The sliding locking mechanism 137 may be controlled by the user via the user interface and controller 446. In some embodiments, the rollers 136 may comprise a sliding actuator and/or roller motor to facilitate electromechanical rolling motion of the rollers and thereby the electromechanical linear motion of the slider 140. The actuator and/or motor may be controlled by the user via the user interface and controller 446, thereby enabling the user to electromechanically control of the liner movement of the slider 140.

The head can further comprise one or more longitudinal supporting elements via which the above described components can be mounted to the housing of the head or to the neck 120. In the present example, the head comprises an elongated support plate 122, carrying the tilting mechanism 131 and extending along the longitudinal axis of the head. The plate 122 can be used for mounting thereon directly or indirectly at different locations along the longitudinal axis of the head LAh any desired components facilitating the operation of the head and/or the cart, e.g. sensors, processors, actuators, gyroscopes, accelerometers, springs or any other electronic and/or mechanical elements, thereby reducing the footprint of the head, e.g., the width of the projection of the head Wh, along the width axis WA.

As indicated above, the surgical robotic device with which the cart 400 can be used is the one described in U.S. Pat. No. 10,463,438. Among other elements, this surgical robotic device comprises a linear unit configured to be releasably attached to a support and to linearly advance the surgical robotic device, with respect to the support. The description of the arrangement allowing such linear advancement in U.S. Pat. No. 10,463,438 is incorporated herein by reference.

For the slider 140 to be enable the fixation thereto of such linear unit, the latter needs to have an mounting portion configured to engage a corresponding mounting portion of the slider. The former and the latter portions can have a number of engageable protrusions and corresponding recesses, configured to provide a stable and secure mounting of the surgical robotic device on the slider while allowing the movement of its linear unit.

Figure 4D:
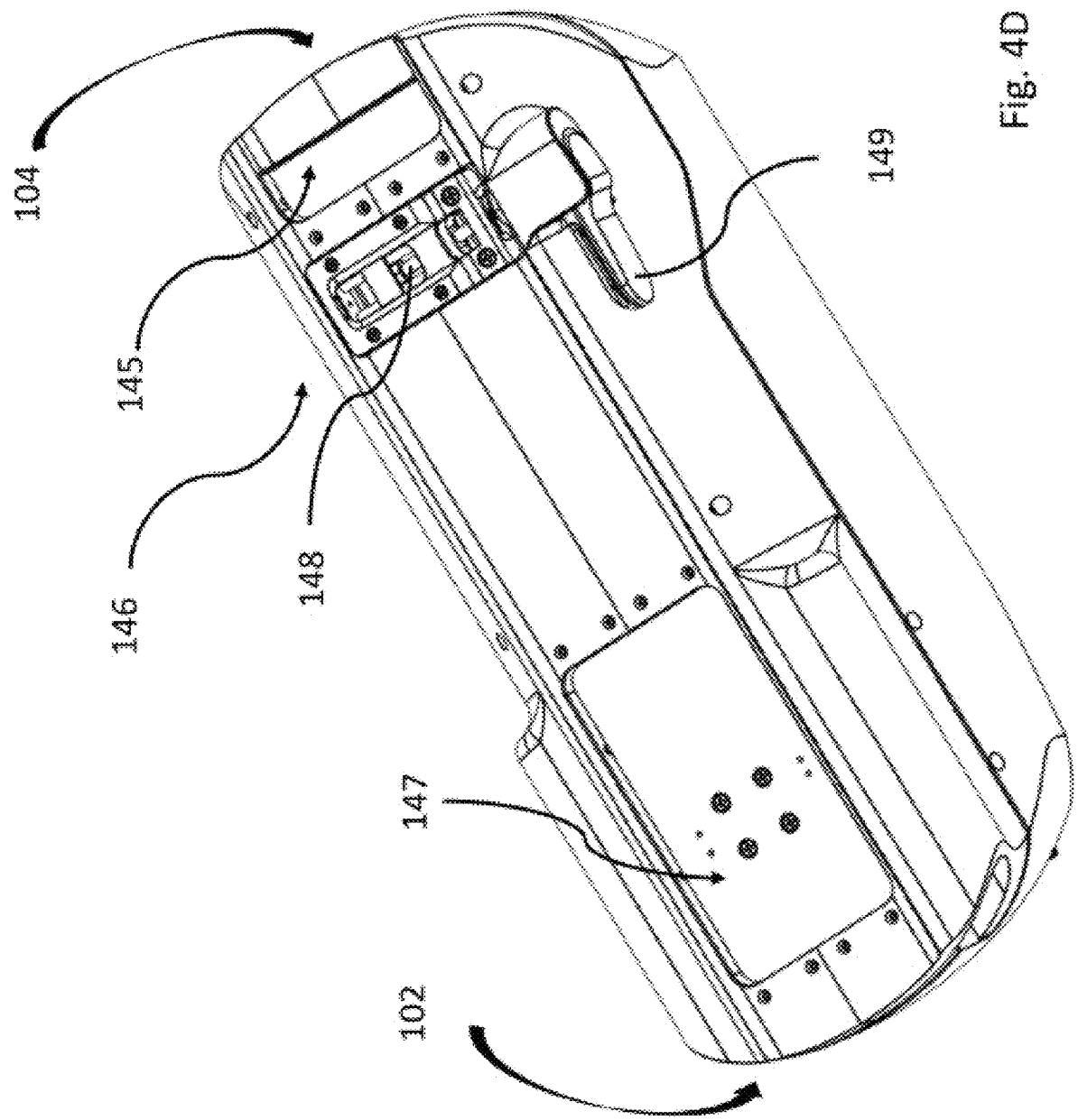
FIG. 4D illustrates one example of an upper perspective view which a slider of the cart shown in FIGS. 4A and 4B can have, according to an embodiment of the presently disclosed subject matter.

In the present example as illustrated in FIG. 4D, the mounting portion of the slider 140 comprises a recessed connecting arrangement 146 and two recessed sockets 145 and 147 positioned at a top surface of the slider at the distal and proximal ends thereof, respectively. The connector arrangement 146 is configured to place and lock a corresponding lockable protrusion of the linear unit of the surgical robotic device, and it comprises an opening 148 which corresponds in shape and/or size to the lockable protrusion. In order to releasably lock the surgical robotic device to the slider 140, the connector 146 comprises a movable lever and/or latch 149 configured to fasten the lockable protrusion of the surgical device once positioned within the opening 148. To better establish the stabilization of the surgical robotic device on top of the slider 140, the surgical robotic device can further comprise two stabilization protrusions configured to be introduced into the sockets 145 and 147. In order to allow the linear unit to advance the surgical robotic within a desired longitudinal range, the sockets 145 and 147 have a larger longitudinal extension than the stabilization protrusions, along the longitudinal axis of the slider 140, as illustrated.

FIGS. 5A and 5B illustrate an example of the use of the cart 400 for positioning a surgical robotic device 500 with respect to the patient, which may lay in a Trendelenburg position or Lithotomy position (both enabling vaginal approach), and a target area location. The user, via the at least one controller 446 is able to control the movement of cart 400, and/or parts thereof, and thereby the positioning of the surgical device 500 in an X-Y-Z Cartesian coordinate system. The at least one controller 446 enables a user to align the surgical device 500 with respect to the patient 550 and/or target area location 552, for example by positioning the cart 400 and/or a part thereof at the required position. For example, by at least setting the length of the neck 120, the horizontal movement of the cart 400 along the reference plane RP, the pivoting of the head 130, i.e. the tilting angle α, and/or the longitudinal movement of the slider 140 along the longitudinal axis LA. Some of the elements in of cart 400 can be controlled manually, e.g. the positioning of the cart 400 along the support surface and reference plane RP and/or the longitudinal movement of slider 140 in the longitudinal direction along the longitudinal axis LA. Whereas defining the height H of the neck 120 in the vertical direction and/or the tilting angle α can be done by using mechanical actuators. It should be noted that in other embodiments, the movement of the cart 400 or parts thereof can be done manually or be at least partially motorized, e.g. by using mechanical actuators.

Once the cart 400 is positioned with respect to the patient 550, e.g. by being manually pushed along the support surface, the user, via controller 446 can electromechanically align the surgical device 500, via movement of the head 130 and/or neck 120 with respect to the treatment target location 552, e.g. by using the height adjusting actuator and/or the tilt adjusting actuator to set height H and the tilting angle α of head 130 and slider 140. The head 130 and slider 140 are positioned to set the surgical robotic device 500 that is mounted thereon or connected to it at a position from which the surgical robotic device 500 can be linearly advanced at a selected angle and/or height into the treatment target location 552. After aligning the surgical device 500 with the treatment target location 552, the user can adjust the distance between the two, e.g. by manually sliding slider 140 in the longitudinal direction along the longitudinal axis LA, thereby linearly advancing the distal end 242 of slider 140 distally while the rest of the elements of cart 400 are still. In some embodiments, for example, to improve control of the liner advancement of the sider 140, the sliding actuator may be added, enabling the user to electromechanically control the sliding motion of the sider 140 via the controller 446. The one or more movable elements of cart 400, such as slider 140 and/or base 110 are configured to move the handle assembly, e.g. by physically pushing it, and/or using one or more movement controllers.

It should be noted that the area surrounding the patient 550 or at least the treatment target location 552 is considered a sterile zone 560, and therefore any element entering that zone should be sterile or at least be covered by a sterile cover, such as a surgical drape. As illustrated in FIG. 5B, the slider 140 along with the surgical robotic device 500, at least in the extreme distal position 220 can enter the sterile zone 560. Therefore, the cart 400 along with the surgical robotic device 500 can be configured for being covered by the sterile cover (not illustrated), which is configured to cover at least the distal portion 104 of the cart 400 along with the surgical robotic device 500 even when slider 140 is positioned at its extreme distal position 220. When the at least one controller 446 is positioned at an extreme proximal end of the cart, e.g. slider 244, or at the proximal end of handle assembly 442, the handle assembly 442 can be shaped and sized to allow, for example, to position the at least one user interface and controller 446 outside of a sterile zone 560, and/or outside the surgical drape. Thereby the handle assembly 442 or at least the controller 446 can be spaced from the sterile zone 560 in the proximal direction and can be used by the user even when the cart 400 or a part thereof and the surgical robotic device are covered by the surgical drape. In other embodiments, the controller 446 can be at least partially remote, e.g. by using a cable or wireless transmissions thereby positioning the controller 446 at a remote location, which can be even farther away from the sterile zone 560.

Figure 6:
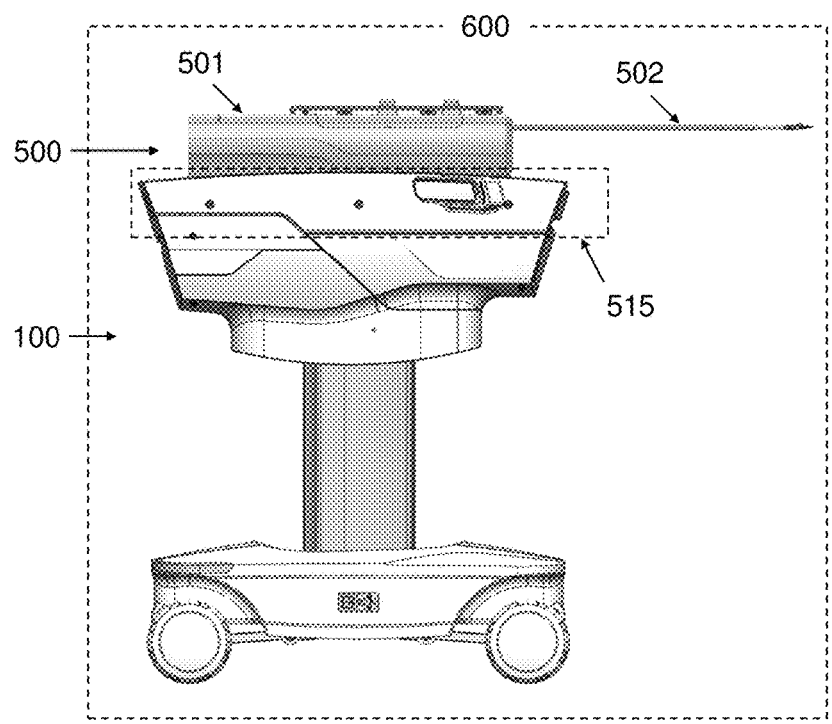
FIG. 6 is a schematic elevation view of a cart supporting a surgical robotic device comprising a surgical arm, according to embodiments of the presently disclosed subject matter.

FIG. 6 illustrates a cart-plus-robotic-device assembly 600 in which an exemplary surgical robotic device 500 is installed on a cart 100, e.g., docked on slider 515. The exemplary surgical robotic device 500 of FIG. 6 comprises a motor-control unit 501 housing motors and gears for controlling one or more surgical arms 502. Each one of the one or more surgical arms 502 is proximally seated, i.e., a proximal portion of each arm 502 is seated, in an arm-receiving volume (not shown) of the motor-control unit 501, as to be secured therein and to be controlled thereby, e.g., by having gears of the surgical arm 502 mesh with corresponding gears in the respective arm-receiving volume(s).

Figures 7A, 7B:
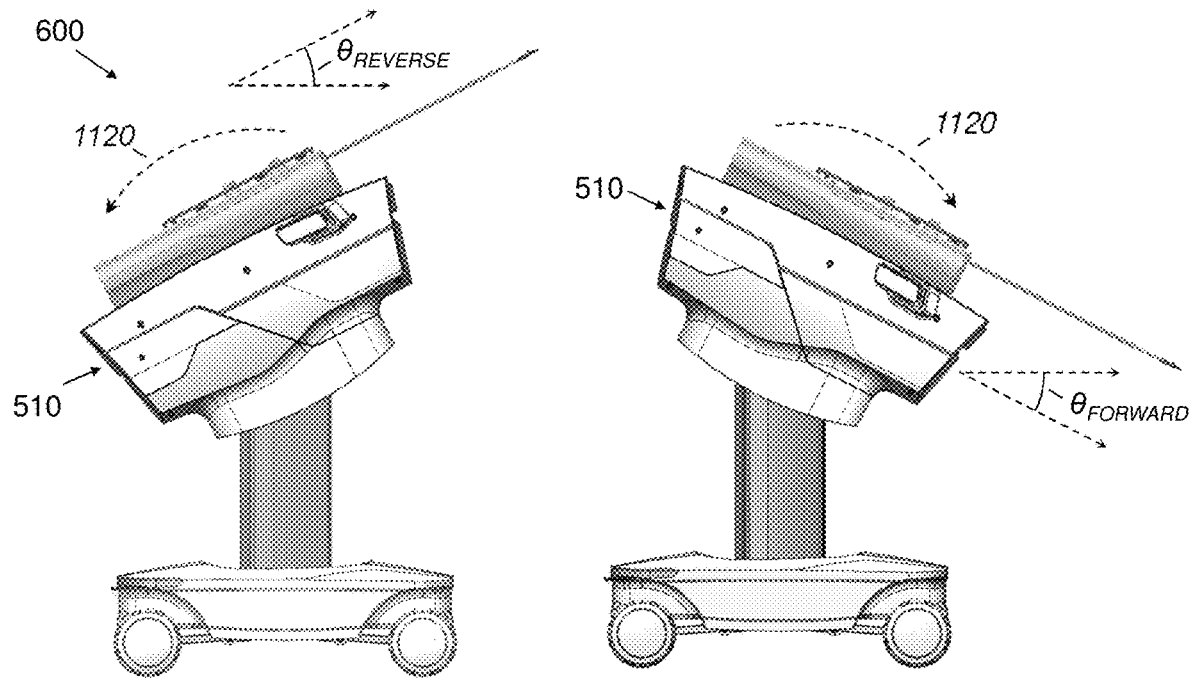
FIGS. 7A and 7B show the cart of FIG. 6, where the head of the cart is pivoted about a pitch axis, according to embodiments of the presently disclosed subject matter.

FIGS. 7A and 7B show an assembly 600, e.g., similar to the cart-plus-robotic-device assembly 600 of FIG. 6 and comprising an upper portion (i.e., the head) 510 configured to pivot about a pitch-axis member (not shown) that mediates between the pillar section 535 and the upper portion 510. The bidirectional pitching of the upper portion 510 is indicated by respective arrows 1120 in both FIGS. 7A and 7B. The pitching is typically a powered pivoting, for example, effected by an onboard motor or other actuator and powered by an external or onboard power source. The pivoting motion can be imparted by any suitable mechanical arrangement such as gears, pistons and/or clutches installed in the cart 100, e.g., any of the mechanisms shown in FIGS. 4A and 4B, and in communication with the pivot-axis member. As illustrated in FIG. 7A, the upper portion 510 can be configured for counterclockwise pitching (i.e., counter-clockwise from the perspective of FIG. 7A) to a maximum pivot angle of $\theta_{REVERSE}$. In embodiments, the pivot angle can correspond to a patient orientation during surgery, such as, e.g., a reverse Trendelenburg position. In embodiments, maximum pivot angle $\theta_{REVERSE}$ is at least 10°, or at least 15°, or at least 20°, or at least 25°, or at least 30°, or at least 35°. As illustrated in FIG. 7B, the upper portion 510 can be configured for clockwise pitching (i.e., clockwise from the perspective of FIG. 7B) up to a maximum pivot angle of $\theta_{FORWARD}$. In embodiments, maximum pivot angle $\theta_{FORWARD}$ is at least 10°, or at least 15°, or at least 20°, or at least 25°, or at least 30°, or at least 35°. In embodiments, the pivot angle can correspond to a patient orientation during surgery, such as, e.g., a Trendelenburg position. In some embodiments, $\theta_{REVERSE}$ and $\theta_{FORWARD}$ are equal, and in other embodiments, based upon specific design choices for the cart 100, they are not.

Figure 8:
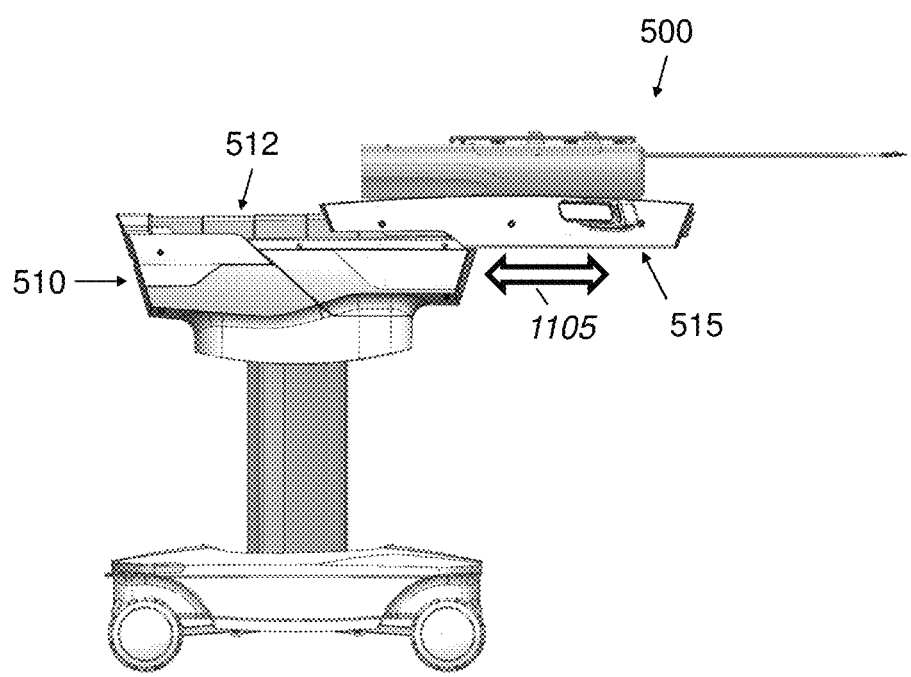
FIG. 8 shows the cart of FIG. 6, where a slider of the cart, bearing the surgical robotic device comprising a surgical arm, is displaced longitudinally in a distal direction, according to embodiments of the presently disclosed subject matter.

FIG. 8 shows cart assembly 600, e.g., similar to the cart-plus-robotic-device assembly 600 of FIG. 6, where the upper portion 510 comprises a slidable docking interface, i.e., slider 515 configured to displace longitudinally, i.e., distally from an initial position of the upper portion 510. The bidirectional displacing of the docking interface 515 is indicated by arrow 1105 in FIG. 8. The longitudinal displacing is typically a powered displacing, for example, effected by an onboard motor or other actuator and powered by an external or onboard power source. The displacing motion can be imparted by any suitable mechanical arrangement such as a piston, or, in the non-limiting example of FIG. 8, a telescoping member 512. The slidable docking interface 515 can be configured to displace distally by up to 120 cm, or up to 100 cm, or up to 80 cm, or up to 60 cm, or up to 40 cm.

The invention claimed is:

1. A cart for positioning a dockable surgical-robotic device, the cart comprising:
   a. a wheeled base section;
   b. an intermediate section extending upwardly from the base section and having a user-adjustable height; and
   c. an upper section mounted atop the intermediate section and pivotable relative thereto throughout a range of inclination angles, the upper section comprising a slidable docking platform for the dockable surgical-robotic device, the docking platform being operative to:
   i. be displaced in a vertical direction when the height of the intermediate section is adjusted, ii. pivot about a pitch axis, together with a non-sliding portion of the upper section, when the upper section is pivoted relative to the intermediate section, and iii. slide longitudinally in a longitudinal sliding direction relative to the non-sliding portion of the upper section, thereby extending a length of the upper section.

2. The cart of claim 1, wherein the docking platform is configured to slide longitudinally to extend a length of the upper section by up to at least half a length of the docking platform.

3. The cart of claim 1, wherein the range of inclination angles is ±30° degrees, said range applying to an inclination of an upper surface of the docking platform relative to a horizontal position.

4. The cart of claim 1, wherein the range of inclination angles is ±30° degrees, said range applying to an angular displacement from a vertical axis extending upward from the intermediate section.

5. The cart of claim 1, further comprising a controller configured to control each one of: the adjusting of the height of the intermediate section, the pivoting of the upper section, and the longitudinal sliding of the docking platform.

6. The cart of claim 1, further comprising a respective activator for effecting each one of: the adjusting of the height of the intermediate section, the pivoting of the upper section, and the longitudinal sliding of the docking platform.

7. The cart of claim 1, wherein the docking platform is configured to fixedly engage a portion of the surgical robotic device.

8. The cart of claim 1, wherein the docking platform comprises a connector mechanism configured to engage the surgical robotic device and reversibly lock the device in place.

9. The cart of claim 1, wherein the non-sliding portion of the upper section includes one or more rails extending in the longitudinal sliding direction for sliding thereupon by the docking platform.

10. The cart of claim 1, wherein a two-dimensional projection of the cart on a floor has a minimum area of no more than 0.3 m², the minimum area being measured when the slidable docking platform is not displaced longitudinally to extend the length of the upper section.

11. The cart of claim 1, wherein the base has an interior configured to receive therein a ballast weight.

12. The cart of claim 1, wherein the intermediate section includes a telescoping member.

13. A kit comprising the surgical positioning cart of claim 1 and the surgical robotic device.

14. The kit of claim 13, wherein the surgical robotic device is docked to the docking platform.

15. A method of operating the cart of claim 1, the method comprising:
   a. displacing the docking platform in the vertical direction by adjusting the height of the intermediate section;
   b. pivoting the docking platform about the pitch axis by pivoting the upper section relative to the intermediate section; and
   c. causing the docking platform to slide in the longitudinal sliding direction relative to the non-sliding portion of the upper section, thereby extending the length of the upper section.

16. A method for positioning a surgical robotic device, the method comprising:
   a. providing a cart comprising a wheeled base section, an intermediate section extending upwardly from the base section and having a user-adjustable height, and a pivotable upper section mounted atop the intermediate section, the upper section comprising a slidable docking platform for the surgical robotic device;
   b. mounting the surgical robotic device on the slidable docking platform, and optionally, locking it thereon;
   c. displacing the upper section in the vertical direction by adjusting the height of the intermediate section;
   d. pivoting the upper section about the pitch axis relative to the intermediate section; and
   e. causing the docking platform to slide in the longitudinal sliding direction relative to the non-sliding portion of the upper section, thereby extending the length of the upper section.

17. The method of claim 16, wherein at least one of the displacing in the vertical direction, the pivoting about the pitch axis, and the sliding in the longitudinal sliding direction, are performed when the surgical robotic device is mounted on the slidable docking platform.

18. The method of claim 17, wherein at least one of the displacing in the vertical direction, the pivoting about the pitch axis, and the sliding in the longitudinal sliding direction, are performed when one or more surgical arms are seated proximally in an arm-receiving section of the surgical robotic device.

19. The method of claim 17, wherein the at least one of the displacing in the vertical direction, the pivoting about the pitch axis, and the sliding in the longitudinal sliding direction is effective to align the one or more surgical arms with a surgical entry site.

20. The method of claim 17, wherein the providing is performed when the surgical robotic device is mounted on the slidable docking platform.

21. The method of claim 16, wherein the mounting the surgical robotic device on the slidable docking platform includes reversibly locking the surgical robotic device to the slidable docking platform.

22. The method of claim 16, wherein the extending the length of the upper section by sliding the docking platform in the longitudinal sliding direction includes sliding the docking platform towards a surgical site.

* * * * *